(12) United States Patent
Schetters et al.

(10) Patent No.: US 9,579,369 B2
(45) Date of Patent: Feb. 28, 2017

(54) VACCINE AGAINST RHIPICEPHALUS TICKS

(71) Applicants: INTERVET INTERNATIONAL B.V., Boxmeer (NL); INTERVET INC., Summit, NJ (US)

(72) Inventors: Theodorus Petrus Maria Schetters, Cuijk (NE); Theodorus Jansen, Venray (NE)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 14/780,115

(22) PCT Filed: Mar. 28, 2014

(86) PCT No.: PCT/EP2014/056248
§ 371 (c)(1),
(2) Date: Sep. 25, 2015

(87) PCT Pub. No.: WO2014/154847
PCT Pub. Date: Oct. 2, 2014

(65) Prior Publication Data
US 2016/0051649 A1 Feb. 25, 2016

(30) Foreign Application Priority Data
Mar. 29, 2013 (EP) .................................... 13161834

(51) Int. Cl.
A61K 39/00 (2006.01)
A61K 39/002 (2006.01)
A61K 49/00 (2006.01)
A61K 9/107 (2006.01)

(52) U.S. Cl.
CPC ........... *A61K 39/0003* (2013.01); *A61K 9/107* (2013.01); *A61K 2039/54* (2013.01); *A61K 2039/545* (2013.01); *A61K 2039/55505* (2013.01); *A61K 2039/55566* (2013.01); *A61K 2039/55577* (2013.01); *A61K 2039/70* (2013.01)

(58) Field of Classification Search
CPC ...................................................... A61K 39/00
USPC ......... 424/9.1, 9.2, 184.1, 185.1, 191.1, 400
See application file for complete search history.

(56) References Cited

PUBLICATIONS

Almazan, C. et al., Control of tick infestations in cattle vaccinated with bacterial membranes containing surface-exposed tick protective antigens, Vaccine, 2012, pp. 265-272, 30.
Almazan, C. et al., Identification and characterization of Rhipicephalus (Boophilus) microplus candidate protective antigens for the control of cattle tick infestations, Parasitol Res, 2010, pp. 471-479, 106.
Carreon, D. et al., Vaccination with BM86, subolesin and akirin protective antigens for the control of tick infestations in white tailed deer and red deer, Vaccine, 2012, pp. 273-279, 30.
De La Fuente, J. et al., A ten-year review of commercial vaccine performance for control of tick infestations on cattle, Animal Health Research Reviews, 2007, pp. 23-28, 8(1), Cambridge University Press.
De La Fuente, J. et al., Identification of protective antigens by RNA interference for control of the lone star tick, *Amblyomma americanum*, Vaccine, 2010, pp. 1786-1795, 28.
De La Fuente, J. et al., Synergistic effect of silencing the expression of tick protective antigens 4D8 and Rs86 in Rhipicephalus sanguineus by RNA interference, Parasitol Res, 2006, pp. 108-113, 99.
De La Fuente, J. et al., Targeting arthropod subolesin/akirin for the development of a universal vaccine for control of vector infestations and pathogen transmission, Veterinary Paraitology, 2011, pp. 17-22, 181.
De La Fuente, J. et al., The tick protective antigen, 4D8, is a conserved protein involved in modulation of tick blood ingestion and reproduction, Vaccine, 2006, pp. 4082-4095, 24.
Extended European Search report for 13161834.0 mailed on Jul. 17, 2013, 5 pages.
Harrington, D. et al., Immunisation with recombinant proteins subolesin and Bm86 for the control of Dermanyssus gallinae in poultry, Vaccine, 2009, pp. 4056-4063, 27.
Hope, M. et al., Experimental vaccination of sheep and cattle against tick infestation using recombinant 5'-nucleotidase, Parasite Immunology, 2010, pp. 135-142, 32.
International Search report, application No. PCT/EP2012/056248, mailed on Jul. 2, 2014,13 pages.
Kemp, D.H. et al., Immunization of cattle against boophilus microplus using extracts derived from adult female ticks: feeding and survival of the parasite on vaccinated cattle, International Journal for Parasitology, 1986, pp. 115-120, vol. 16, No. 2.
Kopp, N. et al., Identification of a synthetic peptide inducing cross-reactive antibodies binding to Rhipicephalus (Boophilus) decoloratus, Rhipicephalus (Boophilus) microplus, Hyalomma anatolicum anatolicum and Rhipicephalus appendiculatus BM86 homologues, Vaccine, 2010, pp. 261-269, 28.
Lee, R.L. and Opdebeeck, J.P., Arthropod vaccines, New vaccines and new vaccine technology, Mar. 1999, pp. 209-226, vol. 13, No. 1.
Merino, O. et al., Control of Rhipicephalus (Boophilus) microplus infestations by the combination of subolesin vaccination and tick autocidal control after subolesin gene knockdown in ticks fed on cattle, Vaccine, 2011, pp. 2248-2254, 20.
Nuttall, P.A. et al., Exposed and concealed antigens as vaccine targets for controlling ticks and tick-borne diseases, Parasite Immunology, 2006, pp. 155-163, 28.

(Continued)

*Primary Examiner* — Rodney P Swartz
(74) *Attorney, Agent, or Firm* — Michael D. Davis

(57) ABSTRACT

The present invention generally relates to the fields of parasitology and immunology, and especially to a vaccine against *Rhipicephalus* ticks. In particular the invention relates to a composition comprising a first and a second protein, in particular Bm86 and Subolesin proteins, including their homologs or immunogenic fragments; to the use of such a composition as a vaccine against *Rhipicephalus* ticks, and to the use of the first and the second isolated proteins for the vaccination of a target against *Rhipicephalus* ticks.

20 Claims, 2 Drawing Sheets

(56) References Cited

PUBLICATIONS

Figure 1:
Figure 1:
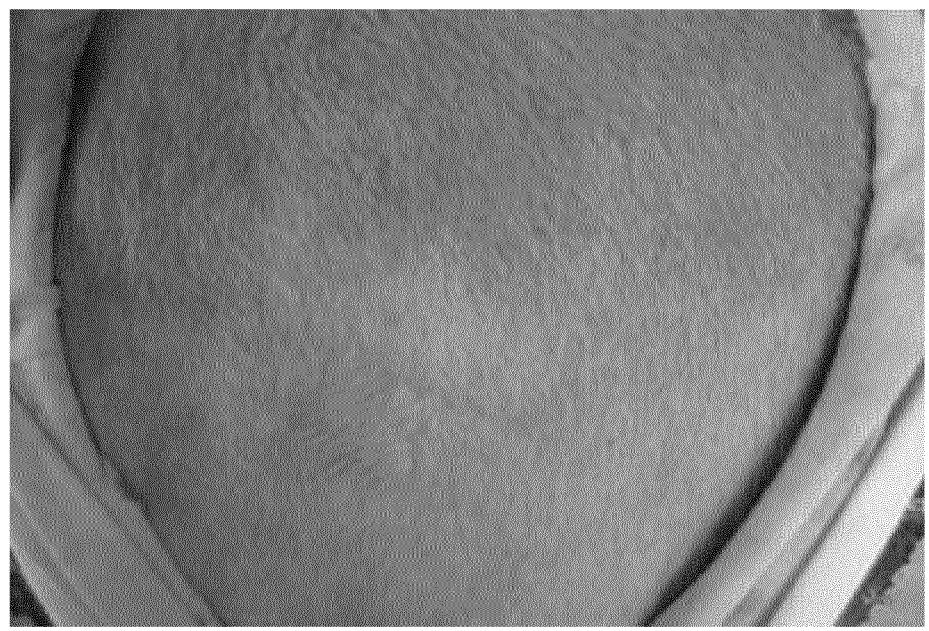

Odongo, D. et al., Vaccination of cattle with TickGARD induces cross-reactive antibodies binding to conserved linear peptides of Bm86 homologues in Boophilus decoloratus, Vaccine, 2007, pp. 1287-1296, 25.

Opdebeeck, J.P., Vaccines against blood-sucking arthropods, Veterinary Parasitology, 1994, pp. 205-222, 54.

Prudencio, C.R. et al., Mapping protective epitopes in the tick and misquito subolesin ortholog proteins, Vaccine, 2010, pp. 5398-5406, 28.

Willadsen, P. et al., Comparative vaccination of cattle against Boophilus microplus with recombinant antigen Bm86 alone or in combination with recombinant Bm91, Parasite Immunology, 1996, pp. 241-246, 18.

Willadsen, P., Anti-tick vaccines, Parasitology, 2004, pp. S367-S387, 129.

Willadsen, P., Antigen cocktails: valid hypothesis or unsubstantiated hope?, Trends in Parasitology, 2008, pp. 164-167, Vo. 24, No. 4.

Willadsen, P., Tick control: Thoughts on a research agenda, Veterinary Parasitology, 2006, pp. 161-168, 138.

SEQUENCE LISTING

```
<160> NUMBER OF SEQ ID NOS: 2

<210> SEQ ID NO 1
<211> LENGTH: 608
<212> TYPE: PRT
<213> ORGANISM: Rhipicephalus microplus

<400> SEQUENCE: 1

Ser Ser Ile Cys Ser Asp Phe Gly Asn Glu Phe Cys Arg Asn Ala Glu
1               5                   10                  15

Cys Glu Val Val Pro Gly Ala Glu Asp Asp Phe Val Cys Lys Cys Pro
            20                  25                  30

Arg Asp Asn Met Tyr Phe Asn Ala Ala Glu Lys Gln Cys Glu Tyr Lys
        35                  40                  45

Asp Thr Cys Lys Thr Arg Glu Cys Ser Tyr Gly Arg Cys Val Glu Ser
    50                  55                  60
```

```
Asn Pro Ser Lys Gly Ser Cys Val Cys Glu Ala Ser Asp Asp Leu Thr
 65                  70                  75                  80

Leu Gln Cys Lys Ile Lys Asn Asp Phe Ala Thr Asp Cys Arg Asn Arg
                 85                  90                  95

Gly Gly Thr Ala Lys Leu Arg Thr Asp Gly Phe Ile Gly Ala Thr Cys
            100                 105                 110

Asp Cys Gly Glu Trp Gly Ala Met Asn Lys Thr Thr Arg Asn Cys Val
        115                 120                 125

Pro Thr Thr Cys Leu Arg Pro Asp Leu Thr Cys Lys Asp Leu Cys Glu
    130                 135                 140

Lys Asn Leu Leu Gln Arg Asp Ser Arg Cys Cys Gln Gly Trp Asn Thr
145                 150                 155                 160

Ala Asn Cys Ser Ala Ala Pro Pro Ala Asp Ser Tyr Cys Ser Pro Gly
                165                 170                 175

Ser Pro Lys Gly Pro Asp Gly Gln Cys Lys Asn Ala Cys Arg Thr Lys
            180                 185                 190

Glu Ala Gly Phe Val Cys Lys His Gly Cys Arg Ser Thr Asp Lys Ala
        195                 200                 205

Tyr Glu Cys Thr Cys Pro Ser Gly Ser Thr Val Ala Glu Asp Gly Ile
    210                 215                 220

Thr Cys Lys Ser Ile Ser Tyr Thr Val Ser Cys Thr Val Glu Gln Lys
225                 230                 235                 240

Gln Thr Cys Arg Pro Thr Glu Asp Cys Arg Val Gln Lys Gly Thr Val
                245                 250                 255

Leu Cys Glu Cys Pro Trp Asn Gln His Leu Val Gly Asp Thr Cys Ile
            260                 265                 270

Ser Asp Cys Val Asp Lys Lys Cys His Glu Glu Phe Met Asp Cys Gly
        275                 280                 285

Val Tyr Met Asn Arg Gln Ser Cys Tyr Cys Pro Trp Lys Ser Arg Lys
    290                 295                 300

Pro Gly Pro Asn Val Asn Ile Asn Glu Cys Leu Leu Asn Glu Tyr Tyr
305                 310                 315                 320

Tyr Thr Val Ser Phe Thr Pro Asn Ile Ser Phe Asp Ser Asp His Cys
                325                 330                 335

Lys Arg Tyr Glu Asp Arg Val Leu Glu Ala Ile Arg Thr Ser Ile Gly
            340                 345                 350

Lys Glu Val Phe Lys Val Glu Ile Leu Asn Cys Thr Gln Asp Ile Lys
        355                 360                 365

Ala Arg Leu Ile Ala Glu Lys Pro Leu Ser Lys Tyr Val Leu Arg Lys
    370                 375                 380

Leu Gln Ala Cys Glu His Pro Ile Gly Glu Trp Cys Met Met Tyr Pro
385                 390                 395                 400

Lys Leu Leu Ile Lys Lys Asn Ser Ala Thr Glu Ile Glu Glu Glu Asn
                405                 410                 415

Leu Cys Asp Ser Leu Leu Lys Asn Gln Glu Ala Ala Tyr Lys Gly Gln
            420                 425                 430

Asn Lys Cys Val Lys Val Asp Asn Leu Phe Trp Phe Gln Cys Ala Asp
        435                 440                 445

Gly Tyr Thr Thr Thr Tyr Glu Met Thr Arg Gly Arg Leu Arg Arg Ser
    450                 455                 460

Val Cys Lys Ala Gly Val Ser Cys Asn Glu Asn Glu Gln Leu Glu Cys
465                 470                 475                 480

Ala Asn Lys Gly Gln Ile Cys Val Tyr Glu Asn Gly Lys Ala Asn Cys
```

-continued

```
                485                 490                 495
Gln Cys Pro Pro Asp Thr Lys Pro Gly Glu Ile Gly Cys Ile Glu Arg
            500                 505                 510

Thr Thr Cys Asn Pro Lys Glu Ile Gln Glu Cys Gln Asp Lys Lys Leu
            515                 520                 525

Glu Cys Val Tyr Lys Asn His Lys Ala Glu Cys Lys Cys Pro Asp Asp
            530                 535                 540

His Glu Cys Ser Arg Gln Pro Ala Lys Asp Ser Cys Ser Glu Glu Asp
545                 550                 555                 560

Asn Gly Lys Cys Gln Ser Ser Gly Gln Arg Cys Val Met Glu Asn Gly
            565                 570                 575

Asn Ala Val Cys Lys Glu Lys Ser Glu Ala Thr Thr Ala Ala Thr Thr
            580                 585                 590

Thr Thr Lys Ala Lys Asp Lys Asp Pro Asp Pro Gly Lys Ser Ser Ala
            595                 600                 605

<210> SEQ ID NO 2
<211> LENGTH: 147
<212> TYPE: PRT
<213> ORGANISM: Rhipicephalus microplus

<400> SEQUENCE: 2

Met Ala Cys Ala Thr Leu Lys Arg Thr His Asp Trp Asp Pro Leu His
1               5                   10                  15

Ser Pro Ser Gly Arg Ser Pro Lys Arg Arg Cys Met Pro Leu Ser
                20                  25                  30

Pro Pro Pro Thr Arg Ala His Gln Ile Asp Pro Ser Pro Phe Gly Asp
            35                  40                  45

Val Pro Pro Lys Leu Thr Ser Glu Glu Ile Ala Ala Asn Ile Arg Glu
        50                  55                  60

Glu Met Arg Arg Leu Gln Arg Arg Lys Gln Leu Cys Phe Gln Gly Ala
65                  70                  75                  80

Asp Pro Glu Ser Gln His Thr Ser Gly Leu Ser Ser Pro Val His Arg
                85                  90                  95

Asp Gln Pro Leu Phe Thr Phe Arg Gln Val Gly Leu Ile Cys Glu Arg
            100                 105                 110

Met Met Lys Glu Arg Glu Ser Lys Ile Arg Glu Glu Tyr Asp His Val
            115                 120                 125

Leu Ser Thr Lys Leu Ala Glu Gln Tyr Asp Thr Phe Val Lys Phe Thr
            130                 135                 140

Tyr Asp Gln
145
```

VACCINE AGAINST RHIPICEPHALUS TICKS

CROSS-REFERENCE TO RELATED APPLICATIONS

This application is a national stage entry under 35 U.S.C. §371 of PCT/EP2014/056248, filed on Mar. 28, 2014, which claims priority under EP 13161834.0, filed on Mar. 29, 2013, the contents of both of which are hereby incorporated by reference in their entireties.

The present invention generally relates to the fields of parasitology and immunology, and especially to a vaccine against *Rhipicephalus* ticks. In particular the invention relates to a composition comprising a first and a second protein, to the use of such a composition as a vaccine against *Rhipicephalus* ticks, and to the use of the first and the second isolated proteins for the vaccination of a target against *Rhipicephalus* ticks.

Ectoparasite infestation is an important concern for human and veterinary health today, as it has significant welfare and economic implications. Ectoparasites are very diverse, but the most relevant pests are arthropods, for example: insects like flies and mosquitoes, or arachnids like ticks and mites. The ectoparasite at one or more stages of its development makes contact with a human or animal host to feed on the host, and this can be a short, an extended and/or a repeated contact. Many ectoparasites, in one or more stages of their development, feed on the blood from a host; therefore they are called haematophores or sanguivores. This type of parasitism has a number of negative effects, which can vary from a simple annoyance to a cause of death. This is because the parasite-host contact involves a variety of mechanical and biological interactions: the ectoparasite's piercing of the skin may cause a rash or an inflammation; the parasite upon its bite may inject with its saliva a number of biological compounds to maintain blood-flow, suppress immune response, and mask sensation, these substances can cause a hypersensitivity reaction; the repeated blood consumption by thousands of ectoparasites over time may cause a host to become anaemic; and also the parasite may be a vector for a microscopic pathogen that can infect the host from the parasite's mouth-parts, saliva, or its faeces. The transmitted pathogen may cause a so-called arthropod vector-borne (Arbo-) disease in the host.

Consequences for the host can be: prolonged stress, parasite-factor induced toxicity, physical damage to hide or skin from bites or secondary infections, anaemia, and/or an infection with a wide variety of transmitted diseases, for example: by bacteria or *Rickettsia*, such as: *Borrelia, Ehrlichia*, or *Anaplasma*; by viruses such as: flavivirus, bunyavirus or reoviruses, causing: dengue, yellow fever, encephalitis, bluetongue, etc.; or by protozoa and helminths such as: *Plasmodium, Babesia, Trypanosomes, Leishmania*, tapeworms, flatworms, nematodal worms, etc. Also there is a real danger of zoonotic spread of such diseases from animal to humans.

An ectoparasite infestation thus affects the general well-being of a human or animal host. For animal hosts of agricultural relevance, this severely affects their economic performance such as in their feed conversion and growth rate, and in the quantity and quality of their production of meat, eggs, milk, wool, hides, and number of offspring.

Arthropod ectoparasites of significant veterinary and zoonotic relevance are the ticks of the *Rhipicephalus* genus. These are hard backed ticks (Ixodidae family) which feed on a variety of mammals, both wild animals such as deer, antelope, and several species of rodents; but also domesticated livestock such as cattle, horses, donkeys, goats, sheep, pigs, and dogs. Some *Rhipicephalus* ticks have a preference for a specific species of host, for example a preference for dogs by *Rhipicephalus sanguineus* (the brown dog tick, or kennel tick). More important economically are the *Rhipicephalus* ticks that feed on bovines, for example: *R. appendiculatus* (brown ear tick), and ticks from the *Boophilus* sub-genus, for example: *R. (Boophilus) microplus* (the Southern cattle tick, which is also known under its old name: *Boophilus microplus*), and *R. (Boophilus) annulatus* (North American tick).

*Rhipicephalus* ticks occur worldwide, but mainly in (sub-)tropical areas. They can be carriers of a wide variety of diseases, some of which are zoonotic, e.g. *Babesia, Theileria, Anaplasma, Coxiella, Borrelia, Rickettsia*, Nairovirus, etc.

Ticks occur in variation with seasonal- or regional circumstances, and have distinct lifecycle stages: egg, larva, nymph, and adult. A full cycle on average takes 2-4 weeks, and each stage displays specific morphological features of the tick body, such as the mouth pieces and dorsal shield. Typical is also the mobility of the ticks, which is reflected in the number of times a tick attaches and detaches from its host. For a review see Barker & Murrell (2002, Exp. & Appl. Acarol., vol. 28, p. 55).

In trying to reduce an infestation by ticks and its consequences, a variety of measures has been applied over time, some more successful than others. Most effective is the use of chemical drugs that repel, kill, or damage the ticks, e.g. acaricides. These may be applied to a host externally e.g. as a spray, pour-on, or by oral or parenteral route, and act on or in the body of the host. Over the last century a wide variety of acaricid drugs for this purpose have been developed.

A major drawback of the use of such chemical anti-parasitics is the development of resistance in the ticks, which makes these compounds less effective over time. As a result it is sometimes necessary to treat livestock every few weeks, which is labour intensive and costly. In addition other concerns apply, such as: fear of toxicity for the user, side-effects for the host, residues in animal products (meat, milk, hides), as well as environmental concerns. This is reviewed by Otranto & Wall (2008, Med. and Vet. Entomol., vol. 22, p. 291).

As an alternative to chemical anti-parasitics, vaccination has been tested for many years, however with moderate success. An ectoparasite vaccine should provide for a reduction in the number of ticks, or in the duration for which they are attached to- or feed from the host. This would also reduce the side effects that the ectoparasite infestation may cause to a host, such as: hide damage, anaemia, toxicity or infection with transmitted diseases. Also, this would reduce the ticks' fecundity, in terms of the number, the weight, and the viability of the eggs that the female tick can produce, which reduces the overall infestation pressure for a herd and/or in a geographical region.

The efficacy of a tick vaccine can be expressed in its 'knock-down effect', meaning the visual reduction in the level of infestation, typically by observing fewer adults. Most likely this is caused by a lethal effect on larvae and nymphs.

The mechanism of action of a vaccine against a heamatophagous ectoparasite is an indirect one: an ectoparasite's host is the target for a vaccination with an antigen from the ectoparasite, so that specific antibodies develop in the target's blood. The ectoparasite that subsequently feeds from the blood of a vaccinated host, thus takes up these antibodies. When the vaccine antigen was derived from an essential biomolecule of the parasite, these antibodies will disturb essential biological processes within the parasite that damage its growth and reproduction (Willadsen, 2004, Parasitology, vol. 129, p. S367).

As the antibodies from the blood meal will require some time to have their effect on the ectoparasite, such a vaccine cannot prevent the initial contact between a vaccinated host and the ectoparasite, like some chemical repellents. However, this type of vaccine can be effective against ectoparasites that remain on the same host for prolonged time (hours, days, weeks), such as *Rhipicephalus* ticks do.

The first vaccines against ectoparasites were rough homogenates of whole parasites, or of specific body parts. Subsequently more specific protein antigens were tested. Mostly these vaccines were used as adjuvated water-in-oil emulsions. These vaccines used either an exposed or a concealed antigen; an exposed antigen being one that is 'seen' by the host's immune system when the ectoparasite makes contact, such as an antigen from its mouth parts or saliva. A concealed antigen being an antigen that is more internal to the ectoparasite and therefore is normally not presented to the host's immune system. Consequently, whereas the immunity against an exposed parasite antigen will be regularly boostered naturally by contact with the ectoparasite; immunity against a concealed parasite antigen will require artificial boosting.

In vaccines against *Rhipicephalus* ticks, concealed, gut-related proteins have been tested in the past. This has led to the development of the only ectoparasite vaccines that are commercially available for veterinary use since the 1990's: TickGARD™ (Intervet, Bendigo, Australia), and Gavac™ (Heber Biotec, Havana, Cuba; Revetmex, Mexico). These vaccines are adjuvanted water-in-oil emulsions for use in bovine targets. They employ a concealed antigen from the midgut of R. (*Boophilus*) *microplus*: Bm86, or its homolog: Bm95, which are produced in a recombinant expression system (*Escherichia coli*, respectively *Pichia pastoris*). Both vaccines reduce the viability and propagation of R. (*Boophilus*) *microplus* ticks to some extent. Therefore these vaccines are mainly used in geographic areas where infestation by acaricid-resistant *Rhipicephalus* ticks is high. For a review see: De la Fuente et al. (2007, Anim. Health Res. Rev., vol. 8, p. 23).

Bm86 is a glycoprotein that is located at the luminal side of the midgut epithelium of R. (*Boophilus*) *microplus* ticks. Bm86 was first described in WO 88/03929. Full length Bm86 has about 650 amino acids, and an apparent Mw of about 89 kDa. The protein has an N-terminal signal sequence, a C-terminal transmembrane region, and a number of EGF-like domains (Lee & Opdebeeck, 1994, Int. J. of Paras., vol. 25, p. 241; Kamau et al., 2011, Insect Mol. Biol., vol. 20, p. 105). Its function in tick biology is not known.

It is assumed that the Bm86-specific antibodies in the blood meal, and maybe complement factors, bind to Bm86 protein on the tick's gut cells and initiate a process that damages the gut (Kemp et al., 1989, Exp. Appl. Acarol., vol. 7, p. 43).

Many amino acid sequences of Bm86 and its homologs are publicly available, e.g. from GenBank, although the naming used is not very consistent: the homologous protein obtained from other *Rhipicephalus* species than from *microplus* can be referred to as Bm86 protein, or as Bm86-like protein, or is designated with its own species code, such as Rs86 for the Bm86 homologous protein obtained from an R. *sanguineus* tick. In literature homologous proteins from different species are sometimes called 'orthologs'.

Homologs of Bm86 have been found in all groups of the Ixodidae family, and their amino acid sequences are quite conserved; within the *Rhipicephalus* genus, the level of amino acid sequence identity between Bm86 homologs is at least about 71% (Nijhof et al., 2010, Int. J. for Parasit., vol. 40, p. 1587). Homologs of Bm86 isolated from ticks of the R. (*Boophilus*) *microplus* species, collected worldwide (Australia, Africa, Mexico, South America), share a level of amino acid sequence identity of at least about 82% (Canales et al., 2008, BMC Biotech., vol. 8, doi: 10.1186/1472-6750-8-14). Because of this high level of conservation, vaccination with a Bm86 homolog from one species of *Rhipicephalus* tick, will also protect against other *Rhipicephalus* ticks.

Protective conserved epitopes from the Bm86 protein have been described (Odongo et al., 2007, Vaccine, vol. 25, p. 1287; Kopp et al., 2010, Vaccine, vol. 28, p. 261).

To improve the efficacy of the Bm86 based ectoparasite vaccines, several possibilities have been considered, only some have been tested.

One option was to improve the formulation of the existing vaccine. This was applied in TickGARD Plus™ (Intervet, Bendigo, Australia) (Anonymous, 2002, Aust. Vet. J., vol. 80, p. 394).

Another option was to use an alternative vaccine antigen, for example from a different part of the tick, such as the mouth parts or the heamolymph. Several lists of potential candidate antigens have been published, for example: Almazan et al. (2003, Vaccine, vol. 21, p. 1492-1501); Willadsen (2004, supra); De la Fuente & Kocan (2006, Paras. Immunol., vol. 28, p. 275); Parizi et al. (2009, Rev. Bras. Parasitol. Vet., vol. 18, p. 1); and Almazan et al. (2010, Paras. Res., vol. 106, p. 471).

Others have proposed to employ combinations; either a combination of chemotherapy and vaccination in an integrated tick-control strategy (Otranto & Wall, 2008, supra), or combinations of antigens in multicomponent vaccines.

Several combinations of two concealed antigens have meanwhile been tested; although in some cases a positive effect was found, no overall improvement of vaccination effect in terms of any added protection was observed. Examples of combinations tested are: Bm86 and Bm91 (a carboxypeptidase from R. (*Boophilus*) *microplus*) (Willadsen et al., 1996, Paras. Immunol., vol. 18, p. 241); Bm86 and BMA7 (a mucin-like glycoprotein) (McKenna et al., 1998, Paras. Immunol., vol. 20, p. 325); and Bm86 and 5' nucleotidase (Hope et al., 2010, Paras. Immunol., vol. 32, p. 135). One study tested the silencing of mRNA from Rs86 (a Bm86 homolog) and Subolesin, using an RNAi approach (de la Fuente et al., 2006, Paras. Res., vol. 99, p. 108).

Subolesin, also known as 4D8, is a protein with an apparent Mw of about 20 kDa, and within the *Rhipicephalus* genus Subolesin has about 161 amino acids. The precise role of this protein is not known, but it is found in different tissues of a tick: the salivary glands, gut, and reproductive tissues. As a concealed antigen, it is characterised even less than Bm86, even though it seems to have a wider presence among arthropods (De la Fuente et al., 2006, Vaccine, vol. 24, p. 4082). Subolesin has a preference for a nuclear localisation in a cell; this concurs with the fact that orthologs of Subolesin found in insects are from the family of Akirin proteins, which are transcription factors (Galindo et al., 2009, Dev. Comp. Immunol., vol. 33, p. 612).

A large number of amino acid sequences of Subolesin homologous proteins are available in GenBank. Commonly they are referred to as Subolesin or 4D8 protein, irrespective of their tick origin. An analysis of Subolesin proteins from various *Rhipicephalus* species, and from a variety of geographic areas revealed these proteins are well conserved and share a level of amino acid sequence identity of at least about 85% (De la Fuente et al., 2006, Vaccine, supra).

Subolesin's function in a *Rhipicephalus* tick has been suppressed experimentally, either by specific antibodies from a Subolesin-vaccinated host, or by gene silencing by an RNAi approach. This significantly interfered with the tick's growth and development, such as its blood meal digestion, oviposition, molting, and survival. Subolesin has been used as a vaccine antigen, and has been suggested for use in combination vaccines with one or more of an abundance of potential vaccine candidates. For a review: De la Fuente et al. (2011, Vet. Path., vol. 181, p. 17). Protective epitopes of Subolesin have been mapped (Prudencio et al., 2010, Vaccine, vol. 28, p. 5398).

Nevertheless, no successful combination vaccine against ticks using Subolesin has been described to date. Interestingly, in their most recent efforts in this field, De la Fuente and co-workers have moved away from testing combination vaccines, and have returned to using single vaccines of Subolesin or Bm86 protein, and recommend combining such a single vaccine with other tick-control measures such as use of acaricides (Carreon et al., 2012, Vaccine, vol. 30, p. 273).

It is remarkable that in spite of all the efforts and suggestions for the use of different antigens and combinations, the results from three decades of research into tick vaccines are at best mediocre. This lead Dr. P. Willadsen, who was the creator of TickGARD™ and is one of the senior scientists in this field, to conclude that: tick vaccines based on antigen cocktails are at best a "valid hypothesis" (though unproven), but in most cases are an "unsubstantiated hope". On the assumption that "such cocktails will show enhanced efficacy", he commented that "The experimental evidence for it, however, is extremely scarce and contradictory." (Willadsen, 2008, Trends in Paras., vol. 24, p. 164-167).

Consequently, the field has an urgent need for a more effective vaccine against *Rhipicephalus* ticks. It is therefore an object of the present invention to overcome disadvantages in the prior art, and to accommodate to this need in the field by providing an improved vaccine against *Rhipicephalus* ticks.

Surprisingly it was found that this object can be met, and consequently disadvantages of the prior art can be overcome, by the use of two protein antigens from *Rhipicephalus* ticks, Bm86 and Subolesin, or their homologs or immunogenic fragments, but only when the two proteins are presented separately to a target's immune system. When the two proteins were combined in a straightforward mixture, only modest levels of antibodies were formed, and mainly against Bm86. Such a vaccination was only partially protective against *Rhipicephalus* ticks placed on a bovine host as a challenge infestation.

However, when Bm86 and Subolesin were presented to the target's immune system simultaneously, but physically separated from each other, the inventors found that the target formed high levels of antibodies against each of the two proteins. These antibodies had a surprisingly favourable combined effect, resulting in a strong immune protection of the vaccinated host against a challenge infestation with *Rhipicephalus* ticks. In some instances an almost complete knock-down effect was observed.

This discovery can now be put to advantageous use in a vaccine against *Rhipicephalus* ticks, essentially in two ways: namely by a single or by a dual administration of these two proteins.

When the two proteins are applied in a single administration, they need to be formulated in such a way that they remain physically separated from each other in the final vaccine composition.

Alternatively, when the two proteins are applied in a dual administration, they need to be administered simultaneously but at different locations on the body, by different routes, or by different methods.

It is not known why the two proteins Bm86 and Subolesin, or their homologs or immunogenic fragments, need to be presented separately to the target's immune system, in order to achieve sufficient stimulation of the humoral immune system for overcoming a tick infestation. Although the inventors do not want to be bound by any theory or model that might explain these observations, they speculate that the cause may be in some form of interference between these two proteins, whereby one is masking the other for the target's immune system.

Consequently, before the present invention a skilled person would employ a straightforward combination of the two proteins, which could not achieve an effective immune protection. The inventors consider this is the reason why there is no prior art describing the use of a combination of Bm86 and Subolesin antigens in a tick vaccine, let alone any successful vaccination result of such use.

In respect of the application of the two protein antigens as a single administration:

In a first aspect the invention relates to a composition comprising a first and a second isolated protein, wherein the first isolated protein comprises an amino acid sequence having an amino acid sequence identity of at least 71% with the amino acid sequence according to SEQ ID NO: 1, and wherein the second isolated protein comprises an amino acid sequence having an amino acid sequence identity of at least 96% with the amino acid sequence according to SEQ ID NO: 2, and wherein the two proteins are physically separated from each other.

Both the first and the second isolated proteins of the composition according to the invention proteins are antigens, and are capable of inducing an immune response. Therefore, a composition according to the invention is an antigenic composition. A composition according to the invention can advantageously be used for the production of a vaccine against *Rhipicephalus* ticks.

The term "comprising" (as well as variations such as "comprise", "comprises", and "comprised") as used herein, refer(s) to all elements, and in any possible combination conceivable for the invention, that are covered by or included in the text section, paragraph, claim, etc., in which this term is used, even if such elements or combinations are not explicitly recited; and does not refer to the exclusion of any of such element(s) or combinations. Consequently, any such text section, paragraph, claim, etc., can also relate to one or more embodiment(s) wherein the term "comprising" (or its variations) is replaced by terms such as "consist of", "consisting of", or "consist essentially of".

For the invention the indications "first" and "second" are used only for ease of reference, and not to indicate any numerical order or dependency.

The term "isolated" is to be interpreted as: isolated from its natural context, by deliberate action or human intervention, e.g. by an in vitro procedure for biochemical purification.

For the invention, a "protein" refers to a molecular chain of amino acids. A protein is not of a specific length, structure or shape, and can if required, be modified in vivo or in vitro by e.g. glycosylation, amidation, carboxylation, phosphorylation, pegylation, or changes in spatial folding. A protein can be a native- or a mature protein, a pre- or pro-protein, or a part of a protein. A protein can be of biologic or synthetic origin. Inter alia, polypeptides and peptides, are included within the definition of protein.

The "amino acid sequence identity" is a well-known way to indicate the evolutionary relatedness between two proteins. It is indicated by the percentage of amino acids that are identical when comparing corresponding positions between two amino acid sequences. Such an alignment is conveniently performed using a computer program, such as the publicly available programs Blast™ or ClustalW™, using default parameters. These programs typically optimise the way two sequences are aligned, and display the region of overlap, with the number and the percentage of identical matches between amino acids. Consequently, the area of overlap found can be the same length as SEQ ID NO: 1 or 2, or smaller, depending on the size of the protein sequence that SEQ ID NO: 1 or 2 are compared with. For the invention the indicated percentages of amino acid sequence identity are based on a comparison to the full length of SEQ ID NO: 1 or 2.

For the invention, SEQ ID NO: 1 represents the partial amino acid sequence from a Bm86 protein identified in a *R. (Boophilus) microplus* tick from Mexico. The complete amino acid sequence of this Bm86 protein is identical to one that is represented in GenBank under accession number: ADQ19685, for an isolate from Texas (USA). SEQ ID NO: 1 has only 608 amino acids, as it is missing the N-terminal 20 amino acids of the protein's native signal sequence, as well as the C-terminal 22 amino acids of its transmembrane region. This truncated form of the Bm86 protein is immunoprotective and can conveniently be produced in vitro, for example in a recombinant expression system.

For the invention the Bm86 protein of SEQ ID NO: 1 serves as a reference for Bm86 protein homologs that can equally be used for the invention. These proteins can be identified by their percentage of amino acid sequence identity to the amino acid sequence of SEQ ID NO: 1.

Therefore, Bm86 homologs are proteins based on, or derived from, proteins from different *Rhipicephalus* species and have a level of amino acid sequence homology to SEQ ID NO: 1 of at least 71% in the region of overlap. This can be determined by alignment of amino acid sequences over the full length of SEQ ID NO: 1, e.g. with proteins in public databases which are at least 608 amino acids in length. For example aligning SEQ ID NO: 1 and the 'gut cell surface glycoprotein' of *R. appendiculatus*, available under GenBank acc. nr.: ADA55445.

Closer related homologs of Bm86 are proteins from ticks of the subgenus *Boophilus*. These generally have an amino acid sequence identity with the full length of SEQ ID NO: 1 of at least 82%, for example when aligning SEQ ID NO: 1 with the 'BD86-like protein' from *R. decoloratus*, available under GenBank acc. nr.: ABY58970.

Still closer related homologs of Bm86 are proteins with amino acid sequences based on, or derived from, ticks of the species *R. (Boophilus) microplus*. These generally have an amino acid sequence identity with the full length of SEQ ID NO: 1 of at least 95%, for example when aligning SEQ ID NO: 1 with the 'Bm86 glycoprotein' of *R. microplus*, available under GenBank acc. nr.: ADQ19687.

Therefore, for the invention, the first isolated protein is a protein comprising an amino acid sequence having an amino acid sequence identity with SEQ ID NO: 1 of at least 71%.

In a preferred embodiment, the first isolated protein for the invention is a protein comprising an amino acid sequence having an amino acid sequence identity with SEQ ID NO: 1 of at least 82%.

In a more preferred embodiment, the first isolated protein for the invention is a protein comprising an amino acid sequence having an amino acid sequence identity with SEQ ID NO: 1 of at least 95%.

In a preferred embodiment of the composition according to the invention, the first isolated protein has an amino acid sequence identity with SEQ ID NO: 1 of at least 71, 73, 75, 80, 82, 85, 87, 90, 92, 93, 95, 96, 97, 98, 99, or even 100%, in that order of preference.

In a further preferred embodiment, the first isolated protein of the composition according to the invention is a Bm86 protein or a homolog thereof.

In a similar way, SEQ ID NO: 2 represents the partial amino acid sequence from a Subolesin (4D8) protein identified in a *R. (Boophilus) microplus* tick from Mexico. SEQ ID NO: 2 is available from GenBank under accession number: ABA62327. SEQ ID NO: 2 has 147 amino acids, as it is missing a C-terminal section of the native Subolesin protein that was not relevant for its immunogenicity. This truncated form of the Subolesin protein is immunoprotective and can conveniently be produced in vitro, for example in a recombinant expression system.

For the invention the Subolesin protein of SEQ ID NO: 2 serves as a reference for Subolesin protein homologs that can equally be used for the invention. These proteins can be identified by their percentage of amino acid sequence identity to the amino acid sequence of SEQ ID NO: 2.

Subolesin proteins were found to be much more conserved than Bm86 proteins, and specifically the part of Subolesin that is in SEQ ID NO: 2 is highly conserved. Therefore, Subolesin homologs are proteins based on, or derived from, proteins from different *Rhipicephalus* species and have a level of amino acid sequence homology to SEQ ID NO: 2 of at least 96% in the region of overlap. This can be determined by alignment of amino acid sequences over the full length of SEQ ID NO: 2, e.g. with proteins in public databases which are at least 147 amino acids in length. For example aligning SEQ ID NO: 2 and the 'protective antigen 4D8' from *R. sanguineus*, available under GenBank acc. nr.: ABA62332.

Even closer related homologs of Subolesin are proteins with amino acid sequences based on, or derived from, proteins originating from ticks of the subgenus *Boophilus* from *Rhipicephalus*, or even from ticks of the species *R. (Boophilus) microplus*. Both of these generally have an amino acid sequence identity with the full length of SEQ ID NO: 2 of at least 99%, for example when aligning SEQ ID NO: 2 with the Subolesin from *R. microplus* that is available under GenBank acc. nr.: AFH57342.

Therefore, for the invention, the second isolated protein is a protein comprising an amino acid sequence having an amino acid sequence identity with SEQ ID NO: 2 of at least 96%.

In a preferred embodiment, the second isolated protein for the invention is a protein comprising an amino acid sequence having an amino acid sequence identity with SEQ ID NO: 2 of at least 99%.

In a preferred embodiment of the composition according to the invention, the second isolated protein has an amino acid sequence identity with SEQ ID NO: 2 of at least 96, 97, 98, 99, or even 100%, in that order of preference.

In a further preferred embodiment, the second isolated protein of the composition according to the invention is a Subolesin protein or a homolog thereof.

For the invention ticks in the genus 'Rhipicephalus', the subgenus 'Boophilus', or the species 'microplus', refer to ticks that are currently classified within the taxonomic groups with those names. This includes also ticks that are sub-classified therefrom in any way, for instance as a sub-species, strain, isolate, genotype, variant or subtype and the like. Such ticks will share the characterising features of their taxonomic group-members such as in their morphologic, genomic, and biochemical characteristics, as well as their biological characteristics such as physiologic, immunologic, or parasitic behaviour. Typically, classification of ticks is based on (electron-) microscopy, and selective nucleotide sequencing or PCR of molecular markers, as known in the field.

It will be apparent to a skilled person that while the ticks that are the subject of the present invention are currently classified in this genus, sub-genus, or species, this is a taxonomic classification that could be subject to change as new insights lead to reclassification into a new or different taxonomic group. This possibility is already evident from the recent phylogenetic reclassification of the genus Boophilus to a sub-genus under Rhipicephalus (Barker & Murrell, 2002, Exp. Appl. Acarol., vol. 28, p. 55). However, as this does not change the ectoparasite involved or its protein repertoire, but only its scientific name or classification, such re-classified ticks remain within the scope of the invention.

Preferred Rhipicephalus ticks for providing (at least one of) the first and the second isolated proteins of the composition according to the invention are Rhipicephalus tick species that infest animals of veterinary relevance such as livestock of companion animals. More preferred are tick species from the genus Rhipicephalus, specifically the species: sanguineus, evertsi, appendiculatus, annulatus, australis, decoloratus, geigyi, kohlsi and microplus.

More preferred are tick species from the subgenus Boophilus from Rhipicephalus, e.g. selected from the R. (Boophilus) species: annulatus, australis, decoloratus, geigyi, kohlsi and microplus.

Most preferred are ticks from the species R. (Boophilus) microplus.

Therefore, in a preferred embodiment the first and the second isolated proteins of the composition according to the invention are derived from, or based on a protein from a tick species of the Boophilus sub-genus from Rhipicephalus.

In an embodiment the first and the second isolated proteins of the composition according to the invention are each derived from a different Rhipicephalus tick species.

For example, the first protein, the Bm86 protein or a homolog thereof, can be derived from R. (Boophilus) microplus, and the second protein, the Subolesin or a homolog thereof, can be derived from R. sanguineus. Such a combination of antigens can provide to a vaccine derived therefrom a broad protection against a number of Rhipicephalus tick species.

Similarly, the two proteins can each be derived from a different R. (Boophilus) microplus tick isolate.

Therefore, in a preferred embodiment, the first and the second isolated proteins of the composition according to the invention are each derived from or based on a different R. (Boophilus) microplus tick isolate.

In a preferred embodiment of the composition according to the invention the first isolated protein comprises an amino acid sequence having an amino acid sequence identity of at least 82% with the amino acid sequence of SEQ ID NO: 1, and/or the second isolated protein comprises an amino acid sequence having an amino acid sequence identity of at least 96% with the amino acid sequence of SEQ ID NO: 2.

In a more preferred embodiment of the composition according to the invention the first isolated protein comprises an amino acid sequence having an amino acid sequence identity of at least 95% with the amino acid sequence of SEQ ID NO: 1, and/or the second isolated protein comprises an amino acid sequence having an amino acid sequence identity of at least 99% with the amino acid sequence of SEQ ID NO: 2.

As will be apparent to a skilled person, the first and the second isolated proteins as described for the invention do not need to be the complete native protein of Bm86, respectively of Subolesin, or their homologs. Rather these proteins may be used in a shortened version or as a fragment, provided these fragments still have adequate immunogenic potential to provide the advantageous effects for the invention. In fact SEQ ID NO: 1 and 2 already present truncated forms of their native parent proteins. Further reductions in length may also be effective, and a skilled person is able to identify those fragments that still provide immune protection. However, in order to be immunogenic a protein fragment needs to be of a minimal length: 8-11 amino acids for MHC I receptor binding, and 11-15 amino acids for MHC II receptor binding (reviewed e.g. by Germain & Margulies, 1993, Annu. Rev. Immunol., vol. 11, p. 403).

Advantageous examples of immunogenic fragments of the first and the second isolated proteins of the composition according to the invention, including their homologs, are fragments comprising at least one of the protective epitopes. It is well within reach of a skilled person to identify such protective epitopes using routine methods e.g. such as by the well-known Pepscan technique (Geysen et al., Proc. Natl. Acad. Sci. USA, 1984, vol. 81, p. 3998), or using computer predictions (Margalit et al., 1987, J. of Immunol., vol. 138, p. 2213).

Examples of such protective epitopes have been described, for example for Bm86 by Odongo et al. (2007, supra), who describe linear cross-protective epitopes corresponding to the amino acid stretches: 8-38 and 512-542 of SEQ ID NO: 1; also Kopp et al. (2010, supra) describe protective epitopes corresponding to the amino acid stretches: 1-22 and 372-396 of SEQ ID NO: 1.

Similarly, for Subolesin, Prudencio et al. (2010, supra) identified the amino acid stretch from 98-123 of SEQ ID NO: 2 as protective epitope.

Therefore in an embodiment, the composition according to the invention comprises an immunogenic fragment from the first or the second isolated protein for the invention.

The immunogenic fragment can be derived from Bm86 or Subolesin, or from a homolog from either of these proteins. The immunogenic fragment may be used instead of, or in addition to, the protein or homolog it is derived from.

In order to enhance the immune response of an immunogenic fragment, this may be combined with or coupled to a carrier molecule. Well known carriers are bacterial toxoids, such as Tetanus toxoid or Diphtheria toxoid; alternatively KLH, BSA, or bacterial cell-wall components (derived from) lipid A, etc. may be used.

A preferred immunogenic fragment for the invention is a fragment from Bm86 or from a homolog thereof, that comprises at least one amino acid stretch of SEQ ID NO: 1 selected from: 1-22, 8-38, 372-396 and 512-542.

A further preferred immunogenic fragment for the invention is a fragment from Subolesin or from a homolog thereof, that comprises the amino acid stretch from 98-123 of SEQ ID NO: 2.

For similar reasons, the first and the second isolated protein of the composition according to the invention can also be longer than the amino acid sequence of SEQ ID NO: 1 or 2, or longer than their native proteins. This may be deliberate or unintended, and is equally acceptable for the invention, provided the amino acid extension does not compromise the protein's immunoprotective ability. Deliberate extension of the proteins may e.g. be used in order to improve expression level, for the purpose of protein-purification or -detection after expression, or to make the protein more immunogenic. An extension can be made in a variety of ways, for example by bio-chemical fusion of amino acids. Most conveniently, this is obtained by modifying the encoding nucleic acid that is used in the expression system. Such fused or extended versions of the first and/or of the second isolated protein of the composition according to the invention are also within the scope of the invention.

For the invention "physically separated" means: comprised by separate physical entities. For the first and the second isolated protein of the composition according to the invention, this means they can be comprised in separate solutions, and/or comprised in- or on separate pharmaceutical carriers.

In embodiments of the separate solutions, a solution is preferably liquid, and the separate solutions can be comprised in one or several containers. For example a composition according to the invention can be an emulsion comprising the separate solutions as separate watery phases.

Therefore, in a preferred embodiment, the composition according to the invention is an emulsion, characterised in that the first and the second protein as described for the invention are comprised in separate watery phases An "emulsion" for the invention is a colloidal liquid system comprising two or more phases, one of which is continuous, and one of which is dispersed in the continuous phase; the dispersion is typically down to micrometer or even nanometer size vesicles.

There are several advantageous embodiments having the two proteins in separate watery phases, for example: in a water-in-oil emulsion, wherein the two proteins are comprised in separate watery phases that are both dispersed within one surrounding oily phase, or: in a water-in-oil-in-water emulsion, wherein the outer and the inner watery phases each comprise one of the two proteins, and are separated by an oily phase.

Alternatively, the two proteins can be separated by using micro-vesicles such as ISCOM's, micelles or liposomes comprising one of the proteins, and being dispersed in a continuous watery phase comprising the other protein.

For embodiments relating to separate pharmaceutical carriers, a variety of compounds and macro-molecular structures are available that can be used to capture one or the other of the two proteins, and in this way present them separately to the immune system of a target upon vaccination.

All these embodiments are well within reach of a person skilled in the art, and all can be put to practice using nothing but routine techniques and standard materials. For example methods and materials for preparing such emulsions are well known in the art, and are described for instance in governmental regulations such as the Pharmacopeia, and in well-known handbooks such as: "Veterinary vaccinology" (P. Pastoret et al. ed., 1997, Elsevier, Amsterdam, ISBN: 0444819681), and: "Remington: the science and practice of pharmacy" (2000, Lippincot, USA, ISBN: 683306472). Details and working examples are outlined in the Examples section.

Such emulsions are typically formed and stabilised by the use of one or more selected surface-active compounds, or surfactants such as emulsifiers, solubilisers, amphiphiles and detergents, or a compound comprising colloidal particles. Well known examples of surfactants are compounds from the families: Span™, Tween™ and Arlacel™. By selecting a surfactant with a desired hydrophilic-lipophilic balance (HLB) value, the different phases of an emulsion can be formed, and remain stable, so that the emulsion does not 'break', even when stored for prolonged time, and at variable temperatures.

The watery phase can be based on purified water, such as water-for-injection, and may comprise salts and/or buffers. The oily phase can be based on any pharmaceutically acceptable oil, for example mineral oils such as Bayol™, Markol™, Montanide™ or light paraffin oil; animal oils such as fish oil, cod liver oil, pristane, squalene or squalane; vegetable oils such as soybean oil, peanut oil, maize oil, cottonseed oil, or sunflower oil; or semi-synthetic oils, such as Miglyol, Cetiol, or Myritol oil.

Ready to use mixtures of an oily phase with an emulsifier are also available commercially, these only require mixing with an antigen in a watery phase. Examples are Montanide ISA 50V2 and Montanide ISA 206 V (Seppic); these comprise a high grade injectable mineral oil and an emulsifier obtained from mannitol and purified oleic acid of vegetable origin.

Therefore in a preferred embodiment of the composition according to the invention, the composition is a water-in-oil emulsion comprising a continuous oily phase and at least two separate watery phases, wherein one of the watery phases comprises the first isolated protein as described for the invention, and another watery phase comprises the second isolated protein as described for the invention.

A "water-in-oil (w/o) emulsion" is well known in the art, and refers to a composition comprising two liquid phases, one dispersed in the other; here: the watery phase is dispersed in the oily phase. Several options for preparing such an emulsion are known. For the invention it is not critical which method is used, as long as in the resulting emulsion the first and the second isolated proteins of the composition according to the invention remain stably physically separated. As an example, two separate w/o emulsions can be prepared, one comprising the first and one comprising the second protein, which can then be combined, gently, so that one continuous oily phase is formed which comprises the two different and separate watery phases.

In another preferred embodiment of the composition according to the invention, the composition is a water-in-oil-in-water emulsion, comprising a continuous outer watery phase, comprising an oily phase, which oily phase comprises at least one internal watery phase, and wherein one protein selected from the first and the second isolated protein as described for the invention is comprised in the outer watery phase, and the other protein from the first and the second isolated protein as described for the invention is comprised in an internal watery phase.

A "water-in-oil-in water (w/o/w) emulsion" is well known in the art, and refers to a composition comprising three liquid phases, dispersed in each other; here: a watery phase is dispersed in the oily phase, which oily phase in turn is dispersed in a watery phase.

Again there are several options for preparing such an emulsion. The method used is not critical, as long as in the resulting emulsion both watery phases, each comprising one of the two proteins of the composition according to the invention, remain separated. For example, a w/o emulsion can be prepared using a watery phase comprising one of the two proteins. This can then be mixed, carefully, with a watery solution comprising the alternate of the two proteins. Under the right conditions a w/o/w emulsion will form, wherein the two proteins are comprised in separate watery phases that are divided by an oily phase. Again, a skilled person will be able to select the necessary compounds and conditions to make the emulsion sufficiently stable.

In yet another preferred embodiment of the composition according to the invention, the first and the second isolated proteins as described for the invention are each comprised by separate pharmaceutical carriers.

For the invention "comprised by separate pharmaceutical carriers" refers to the situation wherein each of the first and the second isolated proteins of the composition according to the invention is attached to a carrier; the attachment should be in such a way that the protein does not readily detaches, as that would not ascertain their separate presentation to a target's immune system.

The term "comprised by" indicates that the protein can be attached in- or on the pharmaceutical carrier in different confirmations, such as on the surface of the carrier, or more internally, such as captured in a grid or gel-like structure, or in macroporous cavities of the carrier. The attachment is noncovalent, and will typically result from a combination of atomic- and ionic interactions such as electrostatic and Van der Waals forces, hydrophobic interactions, and hydrogen bonding.

The term 'separate' aims to indicate that one type, batch or entity of carrier should only comprise one of the two proteins, in order to allow the proteins to be presented to the target's immune system separately. Nevertheless, the carrier that is used for each of the proteins can be the same or different, and the loaded carrier(s) can even be in the same watery phase. This is exemplified below.

Several candidates for a pharmaceutical carrier for use in the invention are known. Examples are pharmaceutically acceptable gels for example from an alum compound, such as an alum-hydroxide gel, or an alum-phosphate gel, or a methylcellulose gel, e.g. Methocel (Dow). A naturally-occurring ionic carbohydrate polymer that is capable of forming a gel upon contact with body fluids, is for example a GelSite™ polymer.

Alternatively, a carrier can be a macro-molecular structure: a 'macro-molecular structure' for use in the invention refers to relatively large molecular structures such as polymeric- or particulate structures, that are of a considerable size, for example more than 1000 Da, or more than 100 nm in size. Well-known examples are: ISCOM™, chitosan, dendromer, alginate, latex-particle, gold-particle, or a synthetic polymer particle, all well-known in the art.

Therefore, in a preferred embodiment of the composition according to the invention, at least one of the pharmaceutical carriers is an alum compound or a macro-molecular structure.

An example of a composition according to the invention wherein the first and the second isolated proteins 'are comprised by separate pharmaceutical carriers' is obtained when a macro-molecular carrier is added to each of two containers, each container comprising a solution with one of the two proteins. After an adequate incubation, the proteins are captured in- or on the carrier. The 'loaded' carriers can for example be washed to remove unbound protein, and can be combined into one solution, which is then a composition according to the invention. In this way the two proteins, even when occurring in the same watery phase, still present themselves separately to the target's immune system upon vaccination. In this example the carrier is the same for the two proteins, but an alternative is to use a different carrier for each of the proteins. It is well within the routine capabilities of a skilled artisan to make and test variations upon this concept, to further optimise the result of such a composition.

A further variation that is within the scope of the invention, is the combination of an emulsion and a pharmaceutical carrier. This can for example be applied in an embodiment wherein one of the first or the second isolated protein for the invention is comprised by a pharmaceutical carrier, e.g. an alum gel, and the protein-loaded alum gel is emulsified with a watery phase into a w/o emulsion.

This may advantageously provide an extra stimulation of a target's immuneresponse to the proteins.

As described, a composition according to the invention can take several forms, and can be prepared in several ways.

Therefore in a further aspect, the invention relates to a method for the preparation of a composition according to the invention, comprising the steps of:

- preparing solutions or pharmaceutical carriers comprising either the first or the second isolated protein as described for the invention, and
- combining these solutions and/or pharmaceutical carriers into one composition, such that the composition comprises both the first and the second isolated protein as described for the invention.

According to the method of the invention, the step of combining the solutions or carriers into one composition may be performed in a variety of ways. For example this can be done (a long time) before the administration, in a laboratory or a pharmaceutical preparation plant. This way of combining provides optimal control over the quality and safety of the resulting combination.

Alternatively, the combining can be done shortly before administration, by admixing of the solution(s) and/or carrier(s), or of ready-made emulsions comprising the solution(s) and/or carrier(s). This can conveniently be done by the person administering the vaccine at the side of the target human or animal to be vaccinated; so called mixing 'on the spot'. For example this comprises the mixing by hand of equal volumes of two w/o emulsions, each containing a different antigen in their watery phase. This results in a w/o emulsion with a continuous oily phase and a dispersed watery phase, having watery phase droplets that contain different and separate antigens, e.g. Bm86 and Subolesin, their homologs, or immunogenic fragments. This method provides optimal flexibility for the selection of solutions to be combined.

Therefore in an embodiment of the method according to the invention, the method comprises the steps of:

- preparing separate emulsions comprising either the first or the second isolated protein as described for the invention, and
- admixing these separate emulsions into a combined emulsion.

The "admixing" is performed by low-intensity mixing, so as not to disrupt the emulsions to be mixed. For example this can be done by low-speed mixing, e.g. at less than 1000 rpm, or by mixing or shaking by hand.

In a preferred embodiment the emulsions are w/o emulsions, as such emulsions are most suitable for mixing on the spot.

As a further alternative for the step of combining the solutions or carriers into one composition, the combining can be done at the moment of administration, by application using a single point injection device that provides for mixing upon inoculation.

In this embodiment the single point injection device has the first and the second isolated protein as described for the invention in separate solutions in separate chambers or containers. Such single point injection devices are well-known in the art, and can e.g. be an electro-mechanical injector with a single needle that is fed from different containers, or can be a combination- or dual syringe with separate chambers that correspond via a joint conduit to a single nozzle to which a needle can be attached. By the combination of the separate solutions in the joint conduit, mixing occurs during the single site injection. Consequently, this qualifies as a single administration of the composition or the vaccine according to the invention, and incorporates the method of the invention.

In a further aspect, the invention relates to a composition obtainable by a method according to the invention, wherein the composition comprises the first and the second isolated proteins as described for the invention physically separated from each other.

The preparation of solutions for use in the method according to the invention can be done in a variety of ways, all well-known to a skilled person. The precise method of preparation is also not critical provided that the resulting composition allows for the advantageous effects of the invention.

For example a solution for the invention can be a watery phase comprising one of the first or the second isolated protein as described for the invention, typically with an appropriate buffer and/or stabiliser.

Also, a solution for the invention can be an emulsion comprising such a watery phase comprising one of the first or the second isolated protein as described for the invention, and an oily phase, for example a light mineral oil.

The standard emulsification of a light mineral oil based w/o emulsion is typically done by emulsification of a watery phase containing an antigen into an oily phase using high shear conditions. Conveniently a high speed mixer e.g. from Silverson can be used, for mixing the water into the oil, e.g. at 4000 rpm for 3 minutes at room temperature. The speed of mixing the two liquid phases and the power and rpm settings of the mixer are controlled and optimised for the volume and the emulsion type that is to be prepared. During mixing the temperature is monitored so that it does not exceed a maximum value, e.g. 40° C. Conveniently such emulsions can be based on commercial ingredients, such as Montanide™ (Seppic), and prepared according to the supplier's instructions.

Appropriate surfactants are used for the emulgation and the stabilisation of the separate phases, for example compounds from the Span™, Tween™, or Arlacel™ families, to control droplet size and -stability. Surfactants are typically used between 0.1 and 10% w/v. A surfactant with a low HLB value (e.g. a Span™) is typically added to the oily phase, and a surfactant with a high HLB value (e.g. a Tween™) is added to the watery phase. The total water-to-oil ratio is preferably between 30:70 and 70:30, and more preferably around 50:50, to have an injectable emulsion with acceptable viscosity.

More complex emulsions can also be made, for example a w/o/w emulsion can e.g. be made by first emulsifying a watery phase (with antigen) into an oily phase using high shear, and subsequently emulsifying this w/o emulsion into a watery phase containing (another) antigen, using low-medium shear. Conveniently an emulsion based on Montanide™ ISA 206 can be used for this purpose.

Also, a watery phase containing an alum-gel loaded antigen can be mixed into an oily adjuvant to generate a w/o or a w/o/w emulsion with enhanced immune stimulation, etc.

Similarly, the preparation of pharmaceutical carriers for use in the method according to the invention can be done in a variety of ways, all well-known to a skilled person. For example, various gels comprising an antigen can be prepared: a methyl cellulose gel can be prepared according to the supplier's instructions, e.g. Methocel™ (Dow). Alternatively it can be dispersed in a non-aqueous solvent, and then water and antigen can be added and mixed.

Also, alginate microspheres can be produced according to well-known protocols: first the alginate is mixed with antigen in water, then microspheres are prepared, e.g. by spray drying, and microspheres are stabilised in a 1% $CaCl_2$, pH 5 solution using high shear conditions.

A chitosan based gel can also be prepared according to the manufacturer's instructions: a 0.5% w/w gel can be prepared using chitosan in water with acetic acid, this can be mixed with 10% sodium sulphate solution and sonicated for dispersion, followed by neutralisation. After sterilisation, this is incubated with an antigen in a watery phase.

Alum gels such as from Alum-hydroxide or Alum-phosphate can be purchased from a variety of suppliers as a 2% or 3% stock solution (e.g. Brenntag, Reheis). The bulk material can be divided out into workable amounts, and sterilised by autoclaving. The gels can be mixed with an antigen by stirring them together for 15 minutes at room temperature, in water with a buffer such as Tris (10 mM) or PBS. Typical end concentration of an alum gel in a final vaccine can be about 0.1% w/v.

The first and the second isolated proteins of the composition according to the invention can be produced or obtained in a variety of ways, but preferably they are produced by an in vitro expression system.

Therefore, in a preferred embodiment of the method according to the invention, the first step comprises the steps of:

expressing a nucleic acid sequence encoding the first or the second isolated protein in an expression system, and harvesting and isolating the expressed protein.

Suitable expression systems are well known and generally available. Examples are recombinant expression systems from bacterial, yeast, insect, plant, or mammalian origin; e.g.: *Escherichia coli, Bacillus subtilis, Lactobacillus* sp., or *Caulobacter crescentus; Sacharomyces cereviseae, Pichia pastoris*; Baculovirus, *Drosophila*; Tobacco; or Hela or CHO cells.

Alternatively, expression may also be performed in so-called cell-free expression systems, for example: the *E. coli* lysate system (Roche), or the rabbit reticulocyte lysate system (Promega corp.).

As is well known in the art, the protein expression system makes use of a nucleic acid sequence encoding the protein of interest. Such a nucleotide sequence may be a gene (i.e. an open reading frame encoding a complete protein), or be a gene-fragment. It may be of natural or synthetic origin.

To drive the expression from the nucleotide sequence, this needs to be under the control of (be operatively linked to) a promoter sequence that is functional within the chosen expression system. Conveniently a wide variety of molecular-biological tools and kits are available for each of the main expression systems that allow the manipulation of the nucleic acid to be expressed.

It is common practice to adapt the nucleotide sequence encoding the desired antigen to the expression system to be used. For example, the inserted gene sequence will preferably lack an N-terminal signal sequence and any transmembrane regions. These can be replaced by a signal of choice that fit the expression system. Similarly, the codon usage of the inserted gene can be adopted to comply with that of the expression system selected, for instance that of E. coli or of insect cells. Typically this is only done by 'silent' mutations such that the amino acids encoded are not altered.

In a preferred embodiment, the first and the second isolated proteins of the composition according to the invention, are produced in different expression systems.

This allows for the separate optimisation of their expression conditions.

In a further preferred embodiment, the Bm86 antigen is produced by a recombinant baculovirus/insect cell expression system, and the Subolesin antigen by a recombinant E. coli expression system.

By employing these particular expression systems, the Rhipicephalus antigens for use as isolated antigens for the invention were favourably produced, and showed enhanced efficacy when applied in a vaccine according to the invention.

Nucleic acids encoding the first or the second isolated protein as described for the invention can be obtained in several ways, for example by isolation from a tick, or via in vitro synthesis, e.g. based on the reverse translation of a certain amino acid sequence. More conveniently the proteins can be synthesised based on published nucleotide sequences available in public databases such as GenBank.

The required molecular-biological techniques, involving cloning, transfection, recombination, selection, and amplification, are well known in the art and are described extensively in handbooks such as: Current Protocols in Molecular Biology, John Wiley & Sons, N.Y. (1989); Basic Methods in Molecular Biology, Elsevier Science Publishing Co., Inc., N.Y. (1986); and: Sambrook & Russell, 2001, in: 'Molecular cloning: a laboratory manual', 3rd ed. New York, USA: Cold Spring Harbour Laboratory Press.

Alternatively, the first and the second isolated proteins of the composition according to the invention can be provided by way of a live recombinant carrier (LRC) micro-organism. This comprises for example embodiments of a recombinant parasite, bacterium, or virus that can be administered to a target human or animal. The LRC micro-organism then survives in the target without apparent harm, and expresses and delivers to the target's immune system the first and the second isolated proteins of the composition according to the invention. Embodiments of such LRC micro-organisms are therefore within the scope of the invention.

The "harvesting and isolating" of the expressed protein, also uses standard procedures, appropriate for the type of expression system that was used. In particular when the expressed protein is secreted by the cells of the expression system, the culture supernatant can be harvested by centrifugation, optionally followed by concentration. Alternatively, when the expressed protein remains within the cells of the expression system, these cells can be harvested, and the protein is produced as an extract, sonicate or lysate of these cells. All this is well-known in the art.

In some embodiments of the composition according to the invention, the composition itself may be suitable for use as vaccine against Rhipicephalus ticks. For example when the oil compound that was used for the preparation of an emulsion according to the invention, already acts as an adequate adjuvant. Also the composition according to the invention may by itself be sufficiently safe, stable and effective to comply with the pharmaceutical requirements of a commercial vaccine.

Nevertheless, the composition according to the invention may require some additives or further processing to turn it into an acceptable and effective vaccine.

Therefore, in a further aspect the invention relates to a composition according to the invention for use as a vaccine against Rhipicephalus ticks.

In a further aspect the invention relates to a composition according to the invention for the vaccination against Rhipicephalus ticks.

In a further aspect the invention relates to the use of a composition according to the invention, for the manufacture of a vaccine against Rhipicephalus ticks.

In a further aspect the invention relates to a vaccine against Rhipicephalus ticks comprising a composition according to the invention, and a pharmaceutically acceptable constituent.

A "vaccine against Rhipicephalus ticks" according to the invention is an immunogenic composition for administration to a suitable target human or animal that can be a host for a Rhipicephalus tick. The vaccine induces in the target an immune response that indirectly affects the Rhipicephalus ticks that have infested the host, by reducing the number, health, and reproductive capacity of these ticks. The vaccine according to the invention may also reduce the number or the severity of the lesions and side-effects caused by the tick infestation, or the target's response thereto.

The term "vaccine" implies the use of an immunologically effective amount of one or more antigenic compound(s) and a pharmaceutically acceptable constituent. The antigenic compounds for the invention are the first and the second isolated proteins of the composition according to the invention.

What constitutes an 'immunologically effective amount' for the vaccine against Rhipicephalus ticks according to the invention depends on the desired effect and on the specific characteristics of the vaccine that is being used. Determination of the effective amount is well within the skills of the routine practitioner, for instance by monitoring the immunological response of the target following vaccination, or after a challenge infestation, e.g. by monitoring the targets' clinical signs and serological parameters, as well as by observation or isolation of ticks on a vaccinated host, and comparing these to responses seen in unvaccinated hosts.

Whether a human or animal host indeed suffers an infestation by Rhipicephalus ticks, and how severely, can be established by a qualified person, such as an experienced livestock breeder or a veterinarian. Because adult and engorged Rhipicephalus ticks are between about 0.5 and about 3 cm in size, they can therefore readily be observed on a host. To determine any infestation by nymphal stages of the Rhipicephalus ticks may require microscopy of a sample obtained from a host. The determination of an observed tick as belonging to the Rhipicephalus genus can be made by a skilled person.

Methods to assess the efficacy of a vaccine according to the invention are thus readily available, and involve observing the difference that a vaccine against Rhipicephalus ticks according to the invention makes to the extent and the consequences of a Rhipicephalus tick infestation, between vaccinated and unvaccinated hosts.

A further advantageous effect of the vaccine according to the invention, is the prevention or reduction of the spread of Rhipicephalus ticks in a geographic area or in a population; this is horizontal spread or environmental infestation. Consequently, the use of a vaccine according to the invention leads to a reduction of the prevalence of Rhipicephalus ticks.

Therefore in a preferred embodiment, the vaccine against Rhipicephalus ticks according to the invention is capable of reducing the prevalence of Rhipicephalus ticks in a geographical area.

A "pharmaceutically acceptable constituent" aids in the effective administration of a vaccine, without causing (severe) adverse effects to the health of the target to which it is administered. Such a solution can for instance be sterile water or a sterile physiological salt solution. In a more complex form the solution can e.g. be a buffer, which can comprise further additives, such as a stabiliser, preservative, or adjuvant. Details and examples are described in well-known handbooks.

The vaccine against Rhipicephalus ticks according to the invention may comprise a stabiliser, e.g. to protect degradation-prone components, or to enhance the shelf-life of the vaccine. Generally stabilisers are large molecules of high molecular weight, such as lipids, carbohydrates, or proteins; for instance milk-powder, gelatine, serum albumin, sorbitol, trehalose, spermidine, Dextrane or polyvinyl pyrrolidone, and buffers, such as alkali metal phosphates. Preferably the stabiliser is free from compounds of animal origin.

The vaccine against Rhipicephalus ticks according to the invention may comprise a preservative, such as thimerosal, merthiolate, phenolic compounds, and/or gentamicin.

It goes without saying that admixing other additives, that are required or beneficial to the pharmaceutical stability or effectiveness of the vaccine according to the invention, are also within the scope of the invention.

When the vaccine against Rhipicephalus ticks according to the invention is not in the form of an emulsion, it may be a watery solution, for example in the embodiment wherein the first and the second isolated proteins of the composition according to the invention are comprised by separate pharmaceutical carriers. In that case the vaccine can be freeze-dried to enhance its stability, and allow prolonged storage at temperatures above freezing.

Procedures for freeze-drying are known to persons skilled in the art, and equipment for freeze-drying at different scales is available commercially.

Therefore, in a more preferred embodiment, the vaccine against Rhipicephalus ticks according to the invention is characterised in that the vaccine is in a freeze-dried form.

To reconstitute a freeze-dried vaccine composition, it is suspended in a physiologically acceptable diluent. This is commonly done immediately before administration, to ascertain the best quality of the vaccine. The diluent can e.g. be sterile water, or a physiological salt solution. The diluent to be used for reconstituting the vaccine can itself contain additional compounds, such as an adjuvant. In another embodiment the freeze dried vaccine may be suspended in an emulsion as outlined in EP 382.271

In a further embodiment of the freeze dried vaccine according to the invention, the diluent for the vaccine is supplied separately from the freeze dried cake comprising the active vaccine composition. In this case, the freeze dried vaccine and the diluent composition form a kit of parts that together embody the present invention.

Therefore, in a preferred embodiment of the freeze dried vaccine against Rhipicephalus ticks according to the invention, the vaccine is comprised in a kit of parts with at least two types of containers, one container comprising the freeze dried vaccine, and one container comprising a watery diluent.

Target for the vaccine against Rhipicephalus ticks according to the invention evidently are human or animal hosts, susceptible to infestation with Rhipicephalus ticks, as described above. However, the age, weight, sex, immunological status, and other parameters of the target to be vaccinated are not critical, although it is evidently favourable to vaccinate healthy targets, and to vaccinate as early as possible to prevent an infestation. As an infestation by Rhipicephalus ticks can be established already at young age, therefore the vaccine against Rhipicephalus ticks according to the invention can be applied within the first 2 weeks after birth.

Preferred targets for the vaccine according to the invention are any companion animal or livestock animal hosts that are susceptible to Rhipicephalus tick infestation. More preferably the target animal is canine, bovine, equine, porcine, caprine, ovine or cervine. Even more preferably, the target animal is bovine, and most preferably the target animal is: taurine cattle (Bos taurus), zebu cattle (Bos indicus), buffalo, bison, yak, or wisent.

The vaccine against Rhipicephalus ticks according to the invention can equally be used as prophylactic or as therapeutic treatment, and interferes both with the establishment and with the progression of an infestation by Rhipicephalus ticks and its consequences.

The vaccine against Rhipicephalus ticks according to the invention can effectively serve as a priming vaccination, which can later be followed and amplified by one or more booster vaccinations, either with the same or with another vaccine against Rhipicephalus ticks.

The schedule for the administration of the vaccine against Rhipicephalus ticks according to the invention, preferably is integrated into existing vaccination schedules for other vaccines for that target.

Preferably the vaccine against Rhipicephalus ticks according to the invention is applied as an annual dose. However, in areas where Rhipicephalus tick infestation is high, re-vaccination at shorter intervals may be required, e.g. after 6 months.

The vaccine against Rhipicephalus ticks according to the invention can be administered in doses containing between 1 and 1000 µg each of the first and of the second isolated protein of the composition according to the invention. Smaller or larger doses can in principle be used; preferably a vaccine dose contains between 10 and 1000 µg of each of the two proteins.

In a series of in vivo seroconversion experiments, different ratios of Bm86 and Subolesin antigens were tested. It was found that the amounts of the two antigens need not be the same; in fact it was found to be favourable to have in an animal dose more of the Subolesin antigen per dose than of the Bm86 protein.

As compared to a particular formulation comprising equal amounts of Bm86 and Subolesin antigens per dose, the antibody titre obtained in calves against Subolesin could be improved when using a similar formulation that comprised an amount of Subolesin antigen was higher than that of Bm86; this did not affect the titre against Bm86.

Therefore, in an embodiment, the vaccine against Rhipicephalus ticks according to the invention comprises the first and the second isolated proteins, whereby the amount of each of the proteins in micrograms per dose differs by more than 5%.

In a preferred embodiment of the vaccine against *Rhipicephalus* ticks according to the invention, the amount of one of the two proteins in micrograms per dose, is about twice that of the other protein.

In a preferred embodiment the vaccine against *Rhipicephalus* ticks according to the invention comprises about 25 µg/dose of Bm86 and about 50 µg/dose of Subolesin.

A vaccine according to the invention comprising such a difference in protein-ratio, demonstrated an enhanced efficacy over a vaccine comprising equal amounts in micrograms per dose of both the proteins.

The vaccine against *Rhipicephalus* ticks according to the invention, is administered in a volume that is acceptable for the target. For instance the volume of one vaccine dose can be between 0.1 and 10 ml. Preferably the volume of one dose is between 0.25 and 5 ml.

The vaccine against *Rhipicephalus* ticks according to the invention can be administered to a target according to methods known in the art. Preferred application is by parenteral route, such as through any route of injection into or through the skin, e.g.: intramuscular, intravenous, intraperitoneal, intradermal, submucosal, or subcutaneous.

The preferred application route for the vaccine against *Rhipicephalus* ticks according to the invention is by intramuscular or by subcutaneous injection.

It goes without saying that the optimal route of application will depend on the specific vaccine formulation that is used, and on the particular characteristics of the target.

It is well within reach of a skilled person to further optimise the vaccine against *Rhipicephalus* ticks according to the invention. Generally this involves the fine-tuning of the efficacy of the vaccine, so that it provides sufficient immune-protection. This can be done by adapting the vaccine dose, volume, or antigen content; by using the vaccine in another form or formulation; by adapting the other constituents of the vaccine (e.g. the stabiliser or the adjuvant); or by application via a different route or method.

The vaccine against *Rhipicephalus* ticks according to the invention may additionally comprise other compounds, such as an adjuvant, an additional antigen, a cytokine, etc. Alternatively, the vaccine against *Rhipicephalus* ticks according to the invention can advantageously be combined with a pharmaceutical component such as an antibiotic, a hormone, or an anti-inflammatory drug.

In a preferred embodiment, the vaccine against *Rhipicephalus* ticks according to the invention is characterised in that it comprises an adjuvant.

An "adjuvant" is a well-known vaccine ingredient that stimulates the immune response of a target in a non-specific manner. Many different adjuvants are known in the art. Examples of adjuvants are: Freund's Complete and -Incomplete adjuvant, vitamin E, non-ionic block polymers and polyamines such as dextran sulphate, carbopol and pyran, aluminium compounds such as Alum-phosphate or Alum-hydroxide, Saponin, etc.

Furthermore, peptides such as muramyldipeptides, dimethylglycine, tuftsin, are often used as adjuvant, and mineral oil e.g. Bayol™ or Markol™, Montanide™ or light paraffin oil, vegetable oils or combination products such as ISA™ from Seppic or DiluvacForte™ can advantageously be used.

A handbook on adjuvants and their uses and effects is: "Vaccine adjuvants" (Methods in molecular medicine, vol. 42, D. O'Hagan ed., 2000, Humana press, NJ, ISBN-10: 0896037355).

Apart from the possible adjuvating effect that may already be provided by components of the composition according to the invention, the vaccine against *Rhipicephalus* ticks according to the invention preferably comprises a saponin adjuvant.

Therefore, in a preferred embodiment the vaccine against *Rhipicephalus* ticks according to the invention comprises a saponin.

In a further preferred embodiment of a vaccine against *Rhipicephalus* ticks according to the invention, the vaccine is an emulsion, wherein saponin is comprised in at least one of the watery phases.

In a further preferred embodiment, a vaccine against *Rhipicephalus* ticks according to the invention is a water-in-oil emulsion wherein Montanide ISA 50V2 is comprised in the oily phase, and saponin Quil A is comprised in at least one of the watery phases.

The combined use of both a Montanide- and a saponin adjuvant was found to induce a more effective immune response compared to when only one of these was used.

A "saponin" is a well-known surface-active glycosidic compound. Commercial products are Quil A™ (Brenntag), Q-vac™ (Biolang), VaxSap™ (Desert King), and Abisco100™ (Isconova). As a saponin is hydrophilic, it can readily be comprised in one or more of the watery phases of the vaccine according to the invention. A saponin adjuvant is preferably comprised in the vaccine according to the invention, at a level between 10 and 10.000 µg/ml, more preferably between 50 and 5000 µg/ml, even more preferably between 100 and 1000 µg/ml.

The inclusion of a saponin as an (additional) adjuvant was found to provide a strong boost to the levels of antibodies that could be induced with a vaccine according to the invention. Partly this was explained by the increase of IgG2a type antibodies that developed in addition to the IgG1 type antibodies that were generated without saponin. In the context of a vaccine against *Rhipicephalus* ticks, the generation of IgG2a type antibodies is all the more favourable as these antibodies are considered to be less dependent of complement factors for their cell-damaging effects, then IgG1 type antibodies.

The vaccine against *Rhipicephalus* ticks according to the invention can advantageously be combined with another antigen, e.g. derived from another pathogen, or an immunologically active compound.

Therefore, in a preferred embodiment the vaccine against *Rhipicephalus* ticks according to the invention comprises an additional immunoactive component.

The "additional immunoactive component" may be an antigen, and/or an immune enhancing substance; either of these may comprise an adjuvant.

The additional immunoactive component when in the form of an antigen may consist of any antigenic component of veterinary importance. It may for instance comprise a biologic or synthetic molecule such as a protein, a carbohydrate, a lipopolysaccharide, or a nucleic acid molecule encoding a proteinaceous antigen. Also a host cell comprising such a nucleic acid, or an LRC micro-organism containing such a nucleic acid molecule, may be a way to deliver a nucleic acid molecule or the additional immunoactive component. Alternatively it may comprise a fractionated or killed micro-organism such as a parasite, bacterium or virus.

The additional immunoactive component(s) may be in the form of an immune enhancing substance e.g. a chemokine, or an immunostimulatory nucleic acid comprising an unmethylated CpG motif. Alternatively, the vaccine against *Rhipicephalus* ticks according to the invention may itself be added to a vaccine.

In a preferred embodiment, the additional immunoactive component is, or is obtained from, a micro-organism infective for a human or an animal that is also a target for the vaccine against *Rhipicephalus* ticks according to the invention.

The advantage of such a combination vaccine is that it not only induces an immune response against *Rhipicephalus* ticks but also against other pathogens while only a single handling of the target for the vaccination is required, thereby reducing vaccination-stress to the target, as well as time- and labour costs.

Examples of such additional immunoactive components are in principle all viral, bacterial, and parasitic pathogens, or an antigen derived thereof, that are applicable for the vaccination of a human or animal that is also a target for the vaccine against *Rhipicephalus* ticks according to the invention.

For example, for porcines: porcine circovirus, porcine reproductive and respiratory syndrome virus, pseudorabies virus, porcine parvo virus, classical swine fever virus, *Mycoplasma hyopneumoniae, Lawsonia intracellularis, E. coli, Streptococcus, Salmonella, Clostridia, Actinobacillus pleuropneumoniae, Pasteurella, Haemophilus, Erysipelothrix, Bordetella, Toxoplasma, Isospora, Trichinella*, etc.

For bovines: *Neospora, Dictyocaulus, Cryptosporidium, Ostertagia, Babesia, Theileria, Anaplasma, Trypanosoma, Cowdria, Toxoplasma*, bovine rotavirus, bovine viral diarrhea virus, bovine coronavirus, bovine infectious rhinotracheitis virus (bovine herpes virus), bovine paramyxovirus, bovine parainfluenza virus, bovine respiratory syncytial virus, rabies virus, bluetongue virus, *Pasteurella haemolytica, E. coli, Salmonella, Staphylococcus, Mycobacterium, Brucella, Clostridia, Mannheimia, Haemophilus, Fusobacterium*, etc.

For ovines or caprines: *Toxoplasma, Neospora, Cowdria, Babesia, Theileria, Anaplasma, Eimeria, Trypanosoma*, peste des petit ruminant virus, bluetongue virus, Schmallenberg virus, *Mycobacterium, Brucella, Clostridia, Coxiella, E. coli, Chlamydia, Clostridia, Pasteurella, Mannheimia*, etc.

For canines: *Ehrlichia, Leishmania donovani*-complex, *Neospora, Anaplasma, Dirofilaria, Dypilidium*, canine parvovirus, canine distemper virus, canine adenovirus types 1 or 2, canine hepatitis virus, canine coronavirus, canine para-influenza virus, rabies virus, feline calicivirus, feline herpesvirus, feline panleucopenia virus, *Clostridium, Hepatozoon, Borrelia burgdorferi, Bordetella bronchiseptica, Chlamydia, Babesia, Theileria*, etc.

A vaccine against *Rhipicephalus* ticks according to the invention is prepared by means well-known to the skilled person.

Therefore, in a further aspect the invention relates to a method for the preparation of a vaccine against *Rhipicephalus* ticks, comprising admixing a composition according to the invention and a pharmaceutically acceptable constituent.

The vaccine against *Rhipicephalus* ticks according to the invention can be prepared by methods as described herein, which are readily applicable by a person skilled in the art. For example, the first and the second isolated proteins as described for the invention can be produced industrially in smaller or larger volumes, in an expression system. The protein is harvested from the expression culture's cells or supernatant. If required for biosafety reasons, the harvested protein product can first be biologically inactivated.

This can be done in several ways, commonly by chemical inactivation, such as with formalin, beta-propiolactone, binary ethyleneimine, or beta-ethanolamine.

A lysate can be produced by physical (French press, sonifier), or by chemical (detergents, chaotropic agents) means. The suspension may be further purified, or be concentrated, e.g. by centrifugation or filtration. The resulting antigen preparation is then combined with pharmaceutically acceptable constituents, formulated into a vaccine, and filled-out into appropriate sized containers. The various stages of the manufacturing process will be monitored by adequate tests, for instance by immunological tests for the quality and quantity of the antigens; by micro-biological tests for inactivation, sterility, and absence of extraneous agents; and ultimately by studies in animals for confirming vaccine efficacy and safety. All these are well known to a skilled person. After completion of the testing for quality, quantity and sterility such vaccine products are released for sale.

General techniques and considerations that apply to the preparation of vaccines are well known in the art and are described for instance in governmental regulations (Pharmacopoeia) and in the well-known handbooks.

Preferably the vaccine against *Rhipicephalus* ticks according to the invention is formulated into a form that is suitable for parenteral injection, i.e. an injectable liquid such as a suspension, solution, dispersion, or emulsion. Commonly such vaccines are prepared sterile, and at physiological pH.

In a further preferred embodiment the vaccine against *Rhipicephalus* ticks according to the invention comprises as first isolated protein 25 µg/dose of baculovirus/insect cell expressed Bm86, and as second isolated protein 50 µg/dose of *E. coli* expressed Subolesin, wherein each isolated protein is comprised in a separate watery phase of a water-in-oil emulsion, whereby each watery phase also comprises saponin Quil A, and the oily phase comprises Montanide ISA 50V2.

As described, the vaccine against *Rhipicephalus* ticks according to the invention can advantageously be applied to a human or animal target that is a susceptible host for infestation by *Rhipicephalus* ticks.

Therefore, in a further aspect the invention relates to a method of vaccination of a target against *Rhipicephalus* ticks, comprising the administration to the target of a vaccine against *Rhipicephalus* ticks according to the invention.

This discovery can now be put to advantageous use in a vaccine against *Rhipicephalus* ticks, essentially in two ways: namely by a single or by a dual administration.

When the two proteins are applied in a single administration, they need to be formulated in such a way that they remain separate from each other in the final vaccine composition, as described above.

Alternatively, the two proteins can be applied in a dual administration, for presentation separately to a target's immune system, in order to induce an immunoprotective reaction against infesting *Rhipicephalus* ticks. This can advantageously be achieved by administration to a target at different locations on the body, by different routes, or by different methods.

Therefore, in a further aspect the invention relates to the first isolated protein as described for the invention for the vaccination of a target against *Rhipicephalus* ticks, characterised in that the protein is administered simultaneous with the second isolated protein as described for the invention, but at different locations on the body, by different routes, or by different methods.

Also, in a further aspect the invention relates to the second isolated protein as described for the invention for the vaccination of a target against *Rhipicephalus* ticks, characterised in that the protein is administered simultaneous with the first isolated protein as described for the invention, but at different locations on the body, by different routes, or by different methods.

In a further aspect the invention relates to the use of the first and the second isolated proteins as described for the invention for the vaccination of a target against *Rhipicephalus* ticks, characterised in that the proteins are administered simultaneous but at different locations on the body, by different routes, or by different methods.

In a further aspect the invention relates to a method of vaccination of a target against *Rhipicephalus* ticks, comprising the administration to the target of the first and the second isolated proteins as described for the invention, characterised in that the administration of the proteins is simultaneous but at different locations on the body, by different routes, or by different methods.

The term "simultaneous" indicates that there is a certain period of time wherein both of the first and the second isolated proteins as described for the invention must have been administered to a target. The purpose of this simultaneous (but separate) administration to the target's immune system, is to induce strong humoral immune responses against each of the proteins. Because a humoral immune response in a mammal can take up to 14 days to develop, therefore both proteins need to be administered to a target within a period of about 14 days. Consequently for the invention 'simultaneous' means: within a period of about 14 days.

Preferably the period for simultaneous administration is shorter, therefore in a preferred embodiment 'simultaneous' means within a period of 12, 10, 8, 7, 6, 5, 4, 3, or 2 days, in that order of preference. Most preferred is simultaneous to mean: within a period of 1 day.

For the invention, the administration to a target of the first and the second isolated proteins as described for the invention needs to be "at different locations on the body, by different routes, or by different methods". This serves to assure the separate presentation of the two proteins to the target's immune system.

For the invention, "different locations on the body" means that the application sites for the administration of (vaccines containing) the first and the second isolated proteins as described for the invention to the target's body, are physically separate. In one embodiment this relates to the use of separate syringes each containing either protein, and these are then used for giving separate injections at separate locations on the target's body, typically more than 1 cm apart, preferably at least 5, 8, 10, 15, 20, or at least 30 cm apart, in that order of preference.

In an alternate embodiment this can refer to the use of a multipoint injection device; the device having more than one injection point, each connected to a separate chamber or container comprising (a vaccine comprising) either of the first or the second isolated protein as described for the invention. Such multipoint injection devices are well-known in the art. For example, in one embodiment this can relate to a combination- or dual syringe with separate chambers, each chamber corresponding to a separate needle; the needles being some distance apart, e.g. between about 0.1-2 cm.

Although the use of a multipoint injection device only requires a single administration action, such an administration of the vaccine according to the invention is nevertheless a dual administration for the invention. This is because the first and the second isolated proteins as described for the invention are administered at different locations on the target's body.

This embodiment differs from the use of a single point injection device as described above.

For the invention, "by different routes" means the use of two different administration routes selected from routes known in the art, and appropriate for the specific target, for example:
 by injection: intramuscular, intravenous, intraperitoneal, intradermal, submucosal, or subcutaneous.
 by topical application as a drop, spray, gel or ointment to the mucosal epithelium of the eye, nose, mouth, anus, or vagina, or onto the epidermis of the outer skin.
 by spray as aerosol, or powder.
 via the alimentary route, by combining with the food, feed or drinking water e.g. as a powder, a liquid, or tablet, or
 by administration directly into the mouth as a liquid, a gel, a tablet, or a capsule, or to the anus as a suppository.

In a preferred embodiment the different routes comprise subcutaneous and intramuscular application.

Also, "by different methods" relates to the various ways in which the first and the second isolated proteins as described for the invention can be formulated. Many of such methods are already listed in the options for different routes, for example: a liquid, a gel, an ointment, a powder, a tablet, or a capsule. In this respect the liquid can be a suspension, solution, dispersion, or an emulsion.

In a preferred embodiment the different methods are selected from an emulsion, a suspension, and a dispersion.

As will be evident to a skilled person, the different ways of application (location, route, and method) can advantageously be combined. Therefore in a preferred embodiment, the first and the second isolated proteins as described for the invention are administered to a target via a combination of differences in their way of application.

For the embodiments of the invention relating to the dual administration, the first and the second isolated proteins as described for the invention can conveniently be offered for sale in a form wherein both proteins are provided in separate containers in their specific pharmaceutical preparations. For ease of use the two containers can be provided in one package, optionally with a diluent, and/or a set of instructions for their administration.

Therefore, in a further aspect the invention relates to a kit of parts comprising at least two containers wherein one container comprises the first isolated protein as described for the invention, and another container comprises the second isolated protein as described for the invention.

The invention will now be further described with reference to the following, non-limiting, examples.

EXAMPLES

1. General Methods and Materials

1.1. Production of Bm86 and Subolesin Antigens

For the various in vivo and in vitro studies performed with Bm86 and Subolesin antigens, a number of different recombinant expression systems have been used. In all cases protein expression was detectable without requiring special modifications. Also all the antigens produced, either from prokaryotic, or eukaryotic, and either from higher- or from lower eukaryotic systems; the antigens were always recognised by specific bovine antisera, and were immunologically active e.g. in assays for artificial feeding of ticks. This indicates that the protein antigens used, Bm86 and Subolesin, do not require complex posttranslational modifications in order to be immunoprotective. Some combinations of antigen and expression system will be described in more detail.

1.1.1. Expression of Subolesin by an *E. coli* Expression System

For expression from *Escherichia coli* bacteria, a transfer/cloning plasmid was used, that was based on the commercial pET14.b plasmid. The Subolesin gene that was expressed in *E. coli* was obtained from a *R.* (*Boophilus*) *microplus* tick from Mexico, and its full sequence is presented in GenBank acc. nr: ABA62327. The expressed protein was the C-terminus truncated 147 amino acid version, essentially as depicted in SEQ ID NO: 2.

DNA primers were constructed for convenient subcloning of the Subolesin gene into the pET plasmid, and for providing it with an N-terminal 6×His fusion-peptide, to facilitate purification and detection. Standard commercial BL21 (DE3)™ *E. coli* cells (Invitrogen) were used for the expression, using standard commercial LB based medium with Ampicillin. Culturing was overnight at 37° C., and 200 rpm.

As the pET type plasmids are set-up for overexpression, the Subolesin antigen was found intracellular in inclusion bodies. These were harvested by centrifugation of the cells, followed by sonification. Next the Subolesin inclusion bodies were denatured using a 6 M Ureum buffer. Then the protein was purified using a His-Trap column, e.g. a Profinia™ IMAC cartridge (BioRad Bio Scale). The eluted Subolesin antigen was concentrated over a 5.0 MWCO PES filter (Vivaspin) by centrifugation, and was dialysed for renaturation against 50 mM MES buffer (morpholino-ethanesulfonic acid) at pH 5.8, over an MWCO 3.5 kDa dialysis membrane (SpectraPore).

This purified Subolesin antigen was further characterised using several techniques. After SDS-PAGE and Coomassie blue staining, the purified Subolesin showed one main band of 20 kDa and some minor bands, probably multimers, at 40, 60, and 80 kDa. In a Western blot, using polyclonal bovine anti-Subolesin antisera, the 20, 40, and 60 kDa bands were specifically recognised.

In an antigen Elisa the specific binding to this Subolesin could be diluted out by titration of the antigen. After the His-trap column purification, the Subolesin antigen was of such high purity that its amount could be determined in a standard BCA protein assay (Pierce), which indicated that a concentration of about 100 mg/l Subolesin could routinely be obtained. The isolated protein was stored frozen at −70° C. until use.

1.1.2. Expression of Subolesin or Bm86 by a *Pichia* Expression System

The expression of the Subolesin or the Bm86 antigen in *Pichia* was done essentially as described (Almazan et al. 2010, and Canales et al., 2008, both supra). In short: the encoding genes were expressed using the commercial pPICZα plasmid (Invitrogen) as transfer vector. This was constructed and amplified in *E. coli*, and then used for the transformation of competent X-33 *P. pastoris* cells. This transfer vector provides for stable integration into the *Pichia* chromosome, under the control of the AOX1 promoter. Depending on the number of gene inserts a specific cell-clone can have a higher or lower expression capacity. Expression was done using standard conditions; first the cells were amplified on basic medium with yeast and soy protein extracts, and glycerol. After amplification the culture was induced to express from the AOX promoter by changing the medium to a 2% methanol medium, and the incubation was continued for another 48 hours.

Both antigens were expressed using a *Pichia* specific signal sequence (MAT alpha prepro), and Bm86 had no transmembrane sequence. Consequently the proteins were produced in the culture supernatant, from which they were concentrated and used for characterisation and vaccine formulation.

1.1.3. Expression of Bm86 by a Baculovirus Expression System

For expression of Bm86 protein in a baculovirus-insect cell expression system, the Bm86 gene from a *R.* (*Boophilus*) *microplus* tick from Mexico was obtained, its sequence is the same as that of GenBank acc. nr. ADQ19685. The encoding nucleotide sequence was optimised to fit the codon usage of a baculovirus without changing the encoded protein, as all mutations made were silent. The gene that was expressed by baculovirus contained the Bm86 signal sequence, but not the transmembrane region; this way the protein was secreted out of the insect cells, and would not remain bound to the cell-membrane. The resulting mature baculovirus expressed Bm86 protein had the amino acid sequence of SEQ ID NO: 1.

The transfervector plasmid used for cloning and expression was the commercial pVL1393 plasmid that provides for expression from the polyhedrin gene promoter. After transfection, recombinant baculoviruses were selected by a number of rounds of plaque purifications. One recombinant was selected for being stable and productive, this was used for scale-up and protein productions. Typically Sf9 or Sf21 insect cells were cultured in commercial SF900 medium, infected at about 0.1 m.o.i., and protein was harvested after 4-5 days of incubation at 28° C. The Bm86 protein as obtained from the insect cell culture supernatant was harvested by centrifugation, inactivation of recombinant baculovirus and concentration over Vivaspin™ membranes.

The purified Bm86 antigen was further characterised using specific anti-Bm86 antisera from rabbits or bovines, by several techniques: a sandwich Elisa, and an SDS-PAGE/Western blot for a band of about 80 kDa. The measurement of the protein amount of Bm86 was troubled to some extent by the high cysteine content of this protein, therefore a standard BCA or Lowry assay gave incorrect amounts. However, standard Bradford or CBB assays both showed reliable measurements, indicating about 400 μg/ml Bm86 protein antigen could routinely be produced in the baculovirus expression system.

1.1.4. Protein Characterisation

To be certain of the identity of the Bm86 and Subolesin proteins produced by an expression system, these were subjected to protein sequence analysis of their tryptic fragments using chromatography and mass spectrometry (Radboud University Proteomics Centre, Nijmegen, NL). Briefly: protein containing gel-strips from preparative SDS-PAGE, were cut out. The proteins were in-gel digested with trypsin, eluted, and analysed on a liquid chromatography column that was coupled to a cyclotron resonance mass-spectrometer. Protein sequences found were analysed for known background and contaminations, and the sequences of the Bm86 and Subolesin proteins were assembled. Both Bm86 and Subolesin were found as the single dominant protein in their respective samples. The coverage for the Subolesin protein sequence was 88%, for Bm86 68%. Nevertheless, the results found matched exactly with the amino acid sequences that were intended to be expressed.

1.2. Serological Assays

For the various serological assays used in the course of the experiments enzyme-linked immuno-sorbent assays (Elisa's) were used. These were performed as standard sandwich (capture) Elisa, and were set up for analysis of either antibody- or of antigen-containing samples. Their basic layout was always the same, in short: a capture antibody was coated to the wells of a titration plate by overnight incubation. The plate was then washed and incubated with an antigen that was recognised specifically by the capture antibody. After incubation and wash, a second, different antibody was added that could also recognise the antigen. After incubation and wash, a third antibody was added, which was specific for the IgG type of the second antibody. The third antibody was conjugated with a horse-radish peroxidase (HRP) enzyme that allows a colour reaction to reveal if any antigen had been bound, by reading in a suitable photo-spectrometric Elisa reader.

For detection of Bm86 protein or -antibodies, the Elisa employed a rabbit IgG anti-Bm86 (*Pichia*) for capture, a cow anti-Bm86 (baculo) second antibody, and a goat anti-bovine IgG-HRP conjugate.

For detection of Subolesin protein or -antibody, the Elisa employed a commercial anti-His-tag antibody for capture, a cow anti-Subolesin second antibody, and a goat anti-bovine IgG-HRP as conjugate.

All procedures used were standard or as recommended by the supplier; similarly all materials used were standard, such as plates, buffers used for coating, incubation, washing or blocking, colouring substrate, etc. Where possible Elisa plate-washing, -reading and result calculation was done by automated method and equipment.

When the Elisa was intended for detection and quantification of antibodies in a sample (potency Elisa), such as in animal sera from a vaccination study, then the antigen used was a reference antigen, and the test serum was titrated as second antibody, along-side a reference second antibody. Conversely, when the Elisa was intended for detection and quantification of antigen material in a sample (antigenic mass Elisa), such as was produced from an expression system, then the test antigen was titrated on the plates, next to a reference antigen sample, and the second antibody was a reference antibody.

When it was relevant to determine if an antibody was of IgG1 or of IgG2 type, then a selective conjugated-antibody was used, e.g. a commercial sheep anti cow-IgG1, or sheep anti cow IgG2a.

The results of these Elisa assays are titre values that are arbitrary, which means their numerical values depend on the specific reference samples and way of dilutions that were used. Therefore their exact value is not relevant, as other ways of performing such an Elisa using a different reference sample will result in a different value. However, because all samples within these experiments were tested the same way, their relative value is relevant, and allows for the comparison of titres of antigen or antibody between samples that were analysed with the same assay.

1.3. Formulation of Vaccines

Emulsions and gels were prepared in principle according to the supplier's instructions, with minor adaptations to accommodate specific equipment- or volume requirements. In short:

Montanide™ ISA50V2 emulsions were prepared entirely according to the instructions of the supplier (Seppic). The Montanide was mixed 50:50 with a watery phase of protein in PBS, by high shear mixing at room temperature, for about 10 minutes. The temperature was monitored not to exceed about 35° C. The Montanide had been sterile-filtered before use. Emulsions were inspected visually and microscopically (1000× amplification) for colour and uniformity.

Montanide ISA50V2+Saponin emulsions were prepared as above, except that QuilA™ saponin was added to the protein-containing watery phase before emulgation. First the QuilA was taken up in PBS to a 10% solution and sterile-filtrated. This was mixed 1:10 with a watery phase of antigen in PBS, and emulsified 50:50 with the Montanide. The final emulsion contained 500 μg/ml Saponin.

Light mineral oil emulsions, using Marcol™ or Drakeol™ as oil were prepared as 40:60 w/o emulsions with proteins in PBS under standard high shear conditions. Surfactants used were 5% Span80™ and 1% Tween80™ (in the final emulsion).

Alum based gels were prepared with (final) 0.15% Alumhydroxide or 0.1% Alumphosphate gels and protein in PBS.

Alum-oil combined emulsions were prepared as w/o combination of the compositions described above, comprising Alumhydroxide- or Alumphosphate-gel with antigen in the watery phase and Montanide ISA50V2 in the oily phase.

2. Vaccination-Challenge Study Using Bm86 and Subolesin Antigens in a Dual Administration Regime

2.1. Study Design

The study was a randomized trial using young bull calves (4-6 months old) of Herford/Holstein mixed breed, obtained from a tick free area, which were assigned randomly to different treatment groups at 5 animals/group. Except for the control group, one dose of test article contained 100 μg of recombinant antigen in a volume of 1 ml of a w/o emulsion. Injections were administered subcutaneously by injection in the neck region. Animals that were vaccinated with more than one protein received injections at separate sites. The initial vaccination was boostered 2 times, with intervals of three weeks.

Three weeks after the last booster, the animals were moved from a common corral to housing in individual pens and received a patched challenge on the flank with 2 species of *Rhipicephalus* ticks, each at opposite sides. Each day infestation sites were checked and any engorged females that had dropped off were collected. A representative number of the collected ticks were incubated to allow oviposition. Tick egg masses were subsequently incubated to measure egress of larvae as a measure of viability.

2.2. Methods

2.2.1. Test Articles

The adjuvant used for this trial was Montanide ISA50V2 (Seppic, France), that had been emulsified into a 50:50 w/o emulsion with a watery phase, under standard conditions. In the control group, the watery phase consisted of standard sterile phosphate buffered saline (PBS). The vaccines contained watery phases with:
- 100 µg Bm86 protein, produced using a *Pichia* expression system. The inserted Bm86 gene had been derived from a Mexican *R. (Boophilus) microplus* tick, without its native signal sequence or transmembrane region.
- 100 µg Subolesin protein, produced using an *E. coli* expression system. The inserted Subolesin gene had been derived from a Mexican *R. (Boophilus) microplus* tick (147 amino acids), and was provided with an N-terminal 6×His fusion peptide.

Vaccine-emulsions were produced sterile, and were kept in glass vials at 2-8° C. until use.

2.2.2. Animals

Calves used were healthy animals, free of *Anaplasma* and *Babesia*, and had an acclimatization period of 4 weeks prior to vaccination. They had an ear tag with a unique number for identification. Feed and water provisions were standard. All animals were observed daily for any abnormalities by a veterinarian.

2.2.3. Treatments

All vaccinations were given subcutaneously in the neck region, with a 1 ml dose, using a 3 ml syringe with a 16 gauge needle. Prior to injection the injection site was shaven. Subsequent injections were given alternating the left and right side of the neck. The dual vaccine was administered at the left and the right side of the neck, on the same day.

Blood sampling was performed at each day of vaccination, but before administration of the vaccine, and prior to the challenge infection, 10 ml of blood was collected from the jugular vein for the preparation of serum. Samples were stored at −20° C. until use.

A transient local swelling was commonly observed at the vaccine-injection site, until about 72 hours p.i.

2.2.4. Tick Challenge

Challenge ticks were a *R. (Boophilus) microplus* from a Mexico isolate, and a *R. (Boophilus) annulatus* from a Texas isolate. The ticks had been maintained as laboratory colonies by feeding on young calves. Engorged ticks were collected and incubated for oviposition and hatching in humidity chambers, at 12-12 hr. light dark cycle, 22-25° C. and 80% relative humidity.

For tick challenge infestation the cattle in the study were shaven at both flanks to mount cells of cotton with glue in which larvae could be placed. To warrant patch infestation, a protective cotton net was mounted around the inoculation site. The next day animals were infested with 250 mg (about 5000) larvae, *R. (Boophilus) microplus* at the right flank, and with the same amount of *R. (Boophilus) annulatus* larvae at the left flank. The nets were then kept closed. Two days after infestation non-adherent larvae were removed. Subsequently, the infested sites were investigated daily for the development of ticks. Any engorged ticks that had dropped off were collected, counted, weighed, and incubated in a humidified (80%) atmosphere at 27° C. to allow egg deposition, development and larval egress.

2.2.5. Evaluation of Results

Antibody Titres

Animal serology determination was by antibody sandwich Elisa as described.

Parasitological Parameters

The total number of engorged ticks recovered from each individual calf (and infestation site) during the infestation period was determined. These numbers were log-transformed to obtain normally distributed data sets, which allowed statistical analysis by parametric assays. Per group, the mean log (number of engorged females), and the group's mean log-average were calculated. Statistical significances of group differences were calculated with ANOVA and Duncan pair wise comparison. Protection was calculated as the reduction in tick numbers compared to the control value, expressed as a percentage.

The weight of each recovered tick was determined and expressed in grams. The egg mass produced per recovered tick (oviposition) was determined and expressed in milligrams. The viability of the eggs (fertility) was determined by weighing the mass of the recovered larvae. Fertility was expressed as the larval mass relative to that of the egg mass, and was expressed as a ratio.

The final and combined effect of the vaccination on the challenge ticks and their progeny, termed: 'total efficacy', was calculated from the combination of the reduction in number of engorged ticks, the reduction in egg mass, and the reduction in fertility, and was expressed as a percentage of reduction in viable progeny.

2.3. Results

2.3.1. Serology

The humoral immune response to the vaccinated antigens proved to be both significant, and antigen specific, as results showed an increase over time. Table 1 presents the titre values just before challenge.

2.3.2. Tick Challenge Responses

Both for the *R. (Boophilus) microplus*, as well as for the *R. (Boophilus) annulatus* tick challenge infestations, there was a clear macroscopic difference in engorged tick numbers among the experimental groups, with a strong reduction in engorged ticks in the vaccinated groups. Several vaccinated animals even showing no engorged ticks at all, whereas on unvaccinated calves, the number of engorged ticks sometimes reached over 600. For illustration of the extend of this difference, FIG. 1 presents photographs from a flank from calves from this study at 23 days post challenge, one was mock vaccinated using adjuvant with PBS, and the other was vaccinated with both Bm86 and Subolesin in a dual application regime.

Based on the number of engorged ticks that could be retrieved from the experimental groups, the differences found were statistically significant (p=0.0164, respectively p=0.0354, on log-transformed data).

The total average % of reduction in tick numbers of both species challenges, as compared to mock vaccinated calves, was about 79% in cattle that were vaccinated only with Bm86, whereas for the groups that had been vaccinated with both Bm86 and Subolesin, the challenge reduction was about 97%.

This very impressive challenge protection, incorporating a reduction of the percentage of reduction in viable progeny, was mainly due to the reduction in numbers of engorging ticks: by preventing ticks maturing to adult stage, this strongly affected the tick's reproduction capabilities.

TABLE 1

Results of vaccination-challenge study.

| Vaccine Ag | | Admin- istration | Serology (Ab titre in 2Log) | | chall. prot. (% reduction) |
|---|---|---|---|---|---|
| Bm86 | Subolesin | | α Bm86 | α Subolesin | |
| Pichia | — | single | 10.2 | <7 | 79 |
| Pichia | E. coli | dual | 10.6 | 10.0 | 97 |
| — | — | control | <7 | <7 | — |

Legend to Table 1:
Ag = antigen; Ab = antibody; chall. prot. = challenge protection.
% reduction = average reduction in the number of engorged ticks (both challenge species)

2.4. Discussion and Conclusions

The results from this in vivo vaccination-challenge study demonstrate that the protective effect of vaccination of cattle against tick infestation using only Bm86 antigen can be improved. In this study the protective effect of the Bm86 antigen is reflected in a reduction in the number of engorging ticks by 79%. This part of the study was a comparative experiment, and replicated the effect that was known for a long time for the commercial single Bm86 antigen vaccines, such as TickGARD. In this case however the protection was above the level commonly observed in the prior art (50-70% reduction), most likely because a larger dose was used (100 instead of 50 μg), and a more intense vaccination-schedule (3 instead of 2 vaccinations in total).

However, the protective effect of this single vaccination can now be improved significantly to a 97% reduction in tick numbers, when cattle are also vaccinated with the Subolesin antigen, in a dual administration regime. These results were obtained using just a standard dosage and formulation.

The challenge protection observed was correlated with the level of antibody response against the Bm86 and Subolesin antigens. The total protective effect (the reduction in viable progeny) against two different species of challenge ticks approached 100%, which transcends the tick species level. In practice this will mean an effective reduction of a herd's infestation pressure.

3. Vaccination-Serology Study Using Bm86 and Subolesin Antigens in a Single Administration Regime

3.1. Summary

An in vivo vaccination study, largely similar in set-up to the one described above was performed, but now the calves' serology was monitored as a measure of their immune-response, and potential for overcoming a challenge infestation. Vaccine antigens used were Bm86 and Subolesin proteins, which were obtained from different expression systems, and were emulsified into different conformations.

Groups of five calves each were vaccinated three times (subcutaneously) with one month intervals. All vaccine preparations were formulated with Montanide ISA 50V2 adjuvant into a 50:50 w/o emulsion. One group (T1) was vaccinated with Bm86 expressed in Pichia pastoris and Subolesin expressed in E. coli formulated as separate vaccines that were injected left and right in the neck region. The second group (T2) was treated similarly but the antigens were derived from baculo virus expression systems. The third group (T3) was vaccinated with baculo virus-expressed Bm86 and Subolesin antigens that were mixed in a single watery phase prior to formulation with adjuvant. The vaccine was divided in two equal aliquots that were injected left and right in the neck region. The fourth group (T4) was vaccinated with baculo virus-expressed Bm86 and Subolesin proteins, each in separate watery phases of a w/o emulsion. The vaccine was divided in two equal aliquots that were injected left and right in the neck region. As control, one group (C) was vaccinated with adjuvant only.

3.2. Methods

3.2.1. Test Articles

Test Group 1:
Dual administration of Bm86 and Subolesin antigens at separate sites. This used 50 μg per dose (1 mL) of Bm86 produced in P. pastoris and 50 μg per dose (1 mL) of Subolesin produced in Escherichia coli, injected at separate sites on the animal. The Bm86 sequence was derived from an Australian tick isolate of R. (Boophilus) microplus.

Test Group 2:
Dual administration of Bm86 and Subolesin antigens at separate sites, using 50 μg per dose (1 mL) of Bm86 produced in a baculo virus and 50 μg per dose (1 mL) of Subolesin produced in a baculo virus, injected at separate sites on the animal.

Test Group 3:
Single administration of Bm86 and Subolesin antigens at the same site, using 50 μg of Bm86 and 50 μg of Subolesin per dose of 2 ml. Each antigen was produced by baculo virus, and the antigens were then combined into a single watery phase, emulsified, and then divided over two equal sized injections at separate sites on the animal.

Test Group 4:
Single administration of Bm86 and Subolesin antigens at the same site, using 50 μg of Bm86 and 50 μg of Subolesin per dose of 2 ml. Each antigen was produced separately by baculo virus, and then emulsified into separate w/o emulsions. In fact the w/o emulsions used were those also used for group T2, and equal parts of these w/o emulsions were mixed by hand shortly before the vaccination. This provided the two antigens in the same w/o emulsion, but each in a separate watery phase. The vaccine volume was then divided over two equal sized injections at separate sites on the animal.

Control Group:
The mock vaccine group received injections of adjuvant only. The vaccination was given as 2×1 ml at separate sites on the animal, to prevent influences of the injection site per se.

3.2.2. Animals

Calves of Ayrshire breed, and of both sexes were used. The calves were about 3 months old, and where clinically healthy. Animals were weighed during the acclimatisation period, and assigned to the treatment groups by random picking from weight-ranked groups. The end result was a random allocation of animals into treatment groups of similar mean weights (about 80 kilograms).

For all the vaccines and for the control, the application was by subcutaneous injection, in the mid caudo-lateral neck, at contra lateral sides, and at a dose volume of 1 ml per injection site.

3.2.3. Statistics

All antibody titre data were log transformed in order to ensure greater normality of the dataset. This allowed the use of parametric statistical analysis of group values. As a result, all means calculated are geometric means unless otherwise noted.

3.2.4. Blood Collection and Processing

Blood samples of all groups were collected weekly for up to 18 weeks. Approximately 10 ml blood was collected in serum-tubes from the left or right vena jugularis. After clot formation, the blood samples were centrifuged and the serum from each tube was decanted or pipetted into labelled cryotubes. Serum samples were then stored at about −40° C., transported on dry ice for Elisa analysis of Bm86- and Subolesin-specific antibody titres.

3.3. Results

3.3.1. Seroconversion

Using antibody capture Elisa's, the antibody response of calves against the proteins that were used for immunization were measured. Depending on the vaccine formulation, different antibody responses against each of the antigens were found. Antibody titres against Bm86 at 2 weeks after the second booster were generally low in all groups of vaccinated animals ranging from 7.2 to 10.8 (in arbitrary Log 2 Elisa titres). Highest antibody titres were found in the calves of group T3, followed by group T4, T1 and T2 in descending order (Table 2).

The highest antibody titres against Subolesin were found in group T1, followed by group T4, T2 and T3 in descending order. Importantly, since the Bm86 and Subolesin antigens used to vaccinate animals from groups T2, T3 and T4 were each derived from a single batch, differences in antibody titres among these groups are related to the vaccine formulation. When the antigens were mixed in the watery phase prior to emulsification in the oil adjuvant (group T3), the response against Subolesin was marginal, although the response against Bm86 was increased. Such interference of the responsiveness against these antigens was not found when the antigens were formulated each in their own watery phase (group T4); the response of this group was very similar to that of cattle that were vaccinated with these antigens as dual administered vaccines (group T2).

The response of cattle against Bm86 produced in *Pichia* (group T1) was similar to that of cattle that received Bm86 produced by baculovirus (group T2). However, the response of cattle against the Subolesin antigen produced by *E. coli* was much higher than that of cattle that were vaccinated with Subolesin produced by baculo virus (group T2; p=0.05, One Way Anova/Duncan).

TABLE 2

Results of vaccination-serology study

| Group | Vaccine Ag Bm86 | Subolesin | Administration | Serology (Ab titre in 2Log) α Bm86 | α Subolesin |
|---|---|---|---|---|---|
| T1 | *Pichia* | *E. coli* | dual | 8.6 | 12.3 |
| T2 | *baculo* | *baculo* | dual | 8.2 | 9.8 |
| T3 | *baculo* | *baculo* | single-combined | 9.7 | 8.2 |
| T4 | *baculo* | *baculo* | single-separate | 8.9 | 9.6 |
| C | — | — | control | 7.2 | 7.3 |

3.4. Discussion and Conclusions

In this in vivo serology study several aspects of a Bm86-Subolesin combination vaccine were tested:

First the effect was studied of the combination of the two antigens Bm86 and Subolesin into a single dosing form. Results show that when Bm86 and Subolesin are combined in a single watery phase (T3), then Subolesin was not recognised well, and the immune response was skewed towards production of antibodies against Bm86. In this group the antibody response against Bm86 was statistically significant higher than that of cattle that were vaccinated with each of the antigens formulated as a separate administration (T1, T2). Conversely, the antibody response against the Subolesin antigen was lower than that of cattle that were vaccinated with the two antigens separately. This effect is unfavourable: although it may be positive to have a higher antibody response against Bm86, this will only provide partial challenge-protection. As was shown in the vaccination-challenge studies (Example 2), a strong protective response requires high levels of antibodies against both Bm86 and Subolesin. Therefore upon a reduction of the Subolesin titre, resulting from the straightforward mixing of the two antigens, no effective immune protection can be obtained.

Remarkably however, when these antigens were present each in a separate watery phase (T4), no interference or skewing of the antibody response was found, and both Bm86 and Subolesin induced a fair titre of specific antibodies. This closely resembled the response observed after the dual administration (T2). Consequently, this demonstrated that in principle it is possible to generate antibody responses against each of the two antigens by using only a single vaccine administration regime, but special care needs to be taken regarding their presentation as separate entities to the target's immune system.

A second goal was to assess the effect of the expression system. Therefore, recombinant Bm86 protein was produced by either *Pichia* or baculovirus expression, and Subolesin was produced by *E. coli* or by baculovirus. It was reassuring to find that all the expression systems used yielded fair amounts of antigen, without special requirements. Using a standard antigenic mass Elisa, the relative amounts of antigen produced were assessed, and the amount of Bm86 selected was about 50 μg, which equalled the dose used in the study of Example 2.

For vaccination of Subolesin antigen, 50 μg was used per dose, which was about half the amount used in the earlier study. The serological response against *E. coli* produced Subolesin was better than that against baculovirus produced Subolesin. Antibody responses against Bm86 were also somewhat less than in the previous trial. It was not immediately clear why, but this was unrelated to the expression system chosen, as the antibody response against Bm86 obtained with baculo virus-produced antigen was comparable to that after immunization with *Pichia*-produced antigen.

It was concluded that the expression system is not critical but that there was room for improving the levels of protective antibody titres obtained, based e.g. on optimization studies for antigen dose and type of adjuvant.

4. In Vitro Tick Feeding Assays

Artificial feeding assays were set up for *Rhipicephalus* ticks, feeding on test samples of bovine blood, as a way to facilitate the assessment of challenge-protective capacity of the levels of anti-Bm86 and/or anti-Subolesin in blood samples. The assays were aimed at detecting a difference in the number of ticks that were engorged, of the total number of ticks placed to feed on a specific blood-sample, and to correlate that to the antigen titre of the blood-sample tested.

Use of these assays helped to reduce the number of experimental animals required. In addition, the in vitro assays proved to be a fast and reliable way of assessing protection against tick challenge, as that is directly related to levels of antibodies against Bm86 and Subolesin in the blood.

4.1. Methods

The assays were done using home built devices, based on the description by Kröber & Guerin (2007, Trends in Paras., vol. 23, p. 445), using a 24 well-plate set-up. *Rhipicephalus* tick larvae were obtained by hatching eggs from adult females that were kept in a laboratory colony, under standard conditions. When about 3 weeks old, about 0.3 gram of larvae in a 50 µl carrier liquid were placed per well, this represented 50-100 larvae; and each sample was tested in 6 wells. The test chambers were covered on one side with a net to prevent escape, and on the other with a feeding membrane that provides access to a sample of blood or serum. The larvae then penetrate the membrane with their mouth-parts and feed from the blood, similar to the natural situation. The test sample was mixed with an antibiotic and an anti-fungal compound for preservation. The test devices were then placed in standard $CO_2$ incubation chambers at 37° C., 5% $CO_2$, and 80% relative humidity.

After incubation for about 72 hours, the chambers were placed at −20° C. to kill the larvae, and then read by microscopy. Scoring was done by deciding if a tick was clearly engorged or not engorged, and counting the numbers of these two groups for each test chamber. Importantly, the person doing the scoring was blinded from the background information of the blood- or serum samples that were tested. These counts gave a final number of the percentage of ticks that were engorged after feeding on a specific sample.

4.2. Results

Figure 2:
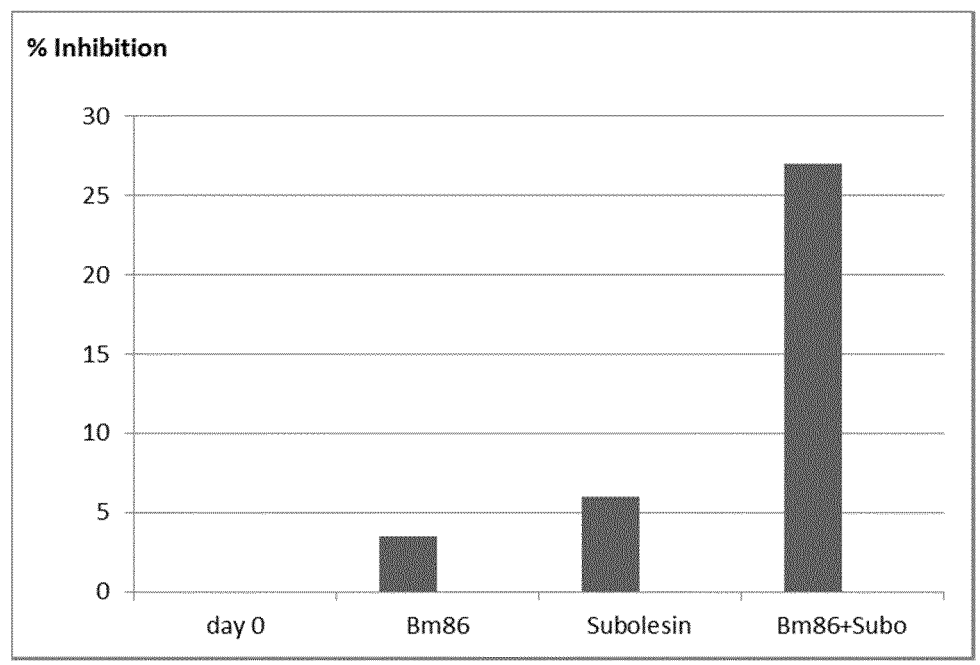

The results of the artificial tick feeding assays, any reduction in the number of engorged ticks for a specific blood- or serum sample tested, were found to correlate well with the Bm86 or Subolesin antibody titre of the samples tested. FIG. 2 represents the results of testing bovine sera in the artificial tick feeding sera. The bovines had been immunised with either Bm86 or with Subolesin antigen in dose finding and adjuvant optimisation studies, as described below. In the particular test displayed in FIG. 2, the sera were obtained after 2 vaccinations.

To test the simultaneous effect on a tick by antibodies against both Bm86 and Subolesin, samples of sera containing these antibodies individually were mixed 1:1. For accurate comparison, the test samples with only Bm86 or only Subolesin antibodies were also diluted 1:1, using calve serum from day 0 (taken before vaccination). The number of engorged ticks found for the day 0 serum sample was set to represent 0% inhibition.

The results indicate a strong increase in inhibition of tick engorgement by the combined Bm86 and Subolesin antisera. The difference between the inhibitions induced by single Bm86 antiserum and by single Subolesin antiserum were not statistically significant.

These results once more reflect the cumulative effect that can be obtained on tick engorgement when sufficiently high levels of antibodies against both Bm86 and Subolesin are present in the tick's blood-meal.

5. Vaccine Optimisation Studies

A number of in vivo vaccination studies have been performed to test various antigen doses, and to optimise the emulsions and the adjuvants used. The studies were assessed by way of serology and testing in tick artificial feeding assays. The studies resulted in formulations that induced very high antibody levels.

One approach was to test the use of Saponin as an adjuvant included into the watery phase of the vaccine emulsions. The saponin will then act in addition to the adjuvating effect that is already induced by the standard oily phase used to make the emulsions according to the invention. In these studies the proteins were used at sub-optimal levels, so that any additional adjuvation effect would stand out more.

In parallel, dose finding studies were performed to test the effect of different amounts of antigen.

For all these studies, the basic set-up were tests in groups of 5 calves (6-8 months old, Frysian/Holstein race, of mixed sex), that were vaccinated and then boostered after 6 weeks. Serum was tested weekly.

For Bm86: antigen amounts of 25, 50, 100, and 200 µg/dose were used. Different formulations were tested with 50 µg Bm86/dose. The different w/o formulations tested were prepared with: Montanide ISA 50V2; Montanide ISA 50V2+Saponin; White Mineral Oil; Alum-hydroxide gel; or Alum-phosphate gel. The Bm86 antigen had been expressed by a baculovirus expression system as described.

For Subolesin: antigen amounts of 12.5, 25, 50, and 100 µg/dose were used. The different formulations (the same types as used for Bm86) were tested with 25 µg Subolesin antigen. The Subolesin antigen had been expressed by an *E. coli* expression system, with an N-terminal His-tag, as described.

Mock vaccination groups were not needed as it was already established these did not develop relevant antibodies.

For both antigens the highest seroresponses were found using either Montanide ISA 50V2+Saponin, or Alum-phosphate gel adjuvants. This could be explained by investigating the IgG profiles, which demonstrated that by these adjuvants, an IgG2a antibody response is generated in addition to an IgG1 response, thereby raising the total level of specific antibodies produced.

The highest antibody levels from the antigen dose finding studies were for Bm86 at 50 µg/dose, and for Subolesin at 100 µg/dose.

Using the standard antibody Elisa assays, the maximal antibody titres obtained in these optimisation studies were determined as: for Bm86: 19 Log 2, and for Subolesin: 18 Log 2 Elisa units.

Considering that these levels of antibodies in the vaccinated targets are well above the levels of about 10 Log 2 Elisa units (as applied in these experiments) that proved protective in the vaccination-challenge study, such vaccinated animals were considered to be effectively protected.

Sera from these studies were used for the in vitro tick feeding assays described above.

6. On-Going In Vivo Vaccination Study Using Optimised Vaccines

An in vivo vaccination study is on-going, in which vaccine formulations with the optimal adjuvant will be tested in combination with the optimal antigen doses. Using essentially the same setup as in the optimisation studies, 6 groups of 5 calves will be immunised with different vaccines, and their serological immune response will be monitored. The test groups are:

Bm86 only:
  50 µg/dose Bm86 antigen, baculovirus expressed, formulated in Montanide ISA 50 V2 with saponin.
Subolesin only:
  50 µg/dose Subolesin antigen, E. coli expressed, formulated in Montanide ISA 50 V2 with saponin.
Bm86+Subolesin dual:
  50 µg/dose Bm86 antigen, baculovirus expressed, formulated in Montanide ISA 50 V2 with saponin administered to one side; and simultaneously, administered to the other side: 50 µg/dose Subolesin antigen, E. coli expressed, formulated in Montanide ISA 50 V2 with saponin.
Bm86+Subolesin single, separate watery phases, 3 groups:
  Bm86 antigen, baculovirus expressed, together with saponin in one watery phase of a Montanide ISA 50 V2 based w/o emulsion; and in another watery phase of the same w/o emulsion: Subolesin antigen, E. coli expressed, together with saponin. This formulation will be tested with three combinations of amounts of each of the antigens: 25, 50 or 100 µg/ml of each of Bm86 or of Subolesin.

The single administration vaccine comprising both antigens, but in separate watery phases will be prepared by mixing, shortly before vaccination, equal volumes of the single w/o vaccines of Bm86 and of Subolesin.

7. Planned In Vivo Vaccination Study Using Optimised Vaccines

Further in vivo vaccination studies are being planned for product development purposes. These will have essentially the same set up but will include an in vivo tick challenge infestation. The vaccines employed will use the optimised dosage and formulation of the Bm86 and Subolesin antigens, as determined in the previous studies. Also these will confirm the necessity of presenting Bm86 and Subolesin proteins separately to a target's immune system.

LEGEND TO THE FIGURES

FIG. 1:
Effect of vaccination with Bm86 and Subolesin antigens upon the number of engorging R. (Boophilus) microplus ticks.
Photographs are from the centre of the lateral side of cows that were subjected to a challenge infestation with R. (Boophilus) microplus larvae, at 23 days after challenge.
  Upper panel: Adjuvant control vaccination
  Lower panel: Vaccinated calf, receiving Bm86 and Subolesin antigens in a dual administration.
  In this animal a complete knock-down was observed.
The net that is visible is to keep the challenge infestation localised as a patch.

FIG. 2:
Results from an artificial tick feeding assay, representing the level of inhibition of tick engorgement that was obtained using a serum sample derived from bovines after two vaccinations with either Bm86 or with Subolesin antigen.
Samples:
  day 0: serum from before vaccination;
  Bm86: serum after vaccination and booster with Bm86 antigen, mixed 1:1 with day 0 serum;
  Subolesin: idem, vaccinated and boostered with Subolesin antigen, also 1:1 with day 0 serum;
  Bm86+Subo: 1:1 combination of the Bm86 and Subolesin sera.

---

The invention claimed is:

1. A composition comprising a first and a second isolated protein, wherein the first isolated protein comprises an amino acid sequence having an amino acid sequence identity of at least 71% with the amino acid sequence according to SEQ ID NO: 1, and wherein the second isolated protein comprises an amino acid sequence having an amino acid sequence identity of at least 96% with the amino acid sequence according to SEQ ID NO: 2, and wherein the two proteins are physically separated from each other by a physical entity selected from the group consisting of being comprised in separate solutions, being comprised in separate pharmaceutical carriers, and being comprised on separate pharmaceutical carriers, and wherein said separate pharmaceutical carriers can be the same or different.

2. The composition of claim 1, wherein the composition is a water-in-oil emulsion comprising a continuous oily phase and at least two separate watery phases, wherein one of the watery phases comprises the first isolated protein, and another watery phase comprises the second isolated protein.

3. The composition of claim 1, wherein the composition is a water-in-oil-in-water emulsion comprising a continuous outer watery phase, and an oily phase comprising at least one internal watery phase, and wherein one protein selected from the first and the second isolated protein is comprised in the outer watery phase, and the other protein from the first and the second isolated protein is comprised in the internal watery phase.

4. The composition of claim 1, wherein the first and the second physically separated proteins are each comprised in a separate pharmaceutical carrier; and wherein said separate pharmaceutical carriers can be the same or different.

5. The composition of claim 4, wherein at least one of the pharmaceutical carriers is an alum compound or a macromolecular structure.

6. A method for the preparation of a composition of claim 1, comprising the steps of:
preparing solutions or pharmaceutical carriers comprising either the first or the second isolated protein, and
combining these solutions or pharmaceutical carriers into one composition or these solutions and pharmaceutical carriers into one composition, such that the composition comprises both the first and the second isolated protein.

7. The method of claim 6, wherein the first step comprises the steps of:
expressing a nucleic acid sequence encoding the first or the second isolated protein in an expression system, and
harvesting and isolating the expressed protein.

8. A vaccine against *Rhipicephalus* ticks comprising the composition of claim 1, and a pharmaceutically acceptable constituent.

9. A method for the preparation of a vaccine against *Rhipicephalus* ticks, comprising admixing the composition of claim 1 and a pharmaceutically acceptable constituent.

10. A method of vaccinating a target against *Rhipicephalus* ticks, comprising administering to the target the vaccine of claim 8.

11. A method of vaccinating a target against *Rhipicephalus* ticks, comprising administering to the target a first and a second isolated protein wherein the first isolated protein comprises an amino acid sequence having an amino acid sequence identity of at least 71% with the amino acid sequence according to SEQ ID NO: 1; wherein the second isolated protein comprises an amino acid sequence having an amino acid sequence identity of at least 96% with the amino acid sequence according to SEQ ID NO: 2; wherein the two proteins are physically separated from each other; and wherein the administration of the first and the second isolated proteins is simultaneous, but at different locations on the body, by different routes, or by different methods.

12. A kit comprising at least two containers, wherein one container comprises a first isolated protein comprising an amino acid sequence having an amino acid sequence identity of at least 71% with the amino acid sequence according to SEQ ID NO: 1 and another container comprises a second isolated protein comprising an amino acid sequence having an amino acid sequence identity of at least 96% with the amino acid sequence according to SEQ ID NO: 2.

13. A vaccine against *Rhipicephalus* ticks comprising the composition of claim 5, and a pharmaceutically acceptable constituent.

14. A vaccine against *Rhipicephalus* ticks comprising the composition of claim 4, and a pharmaceutically acceptable constituent.

15. A vaccine against *Rhipicephalus* ticks comprising the composition of claim 3, and a pharmaceutically acceptable constituent.

16. A vaccine against *Rhipicephalus* ticks comprising the composition of claim 2, and a pharmaceutically acceptable constituent.

17. A method of vaccinating a target against *Rhipicephalus* ticks, comprising administering to the target the vaccine of claim 16.

18. A method of vaccinating a target against *Rhipicephalus* ticks, comprising administering to the target the vaccine of claim 15.

19. A method of vaccinating a target against *Rhipicephalus* ticks, comprising administering to the target the vaccine of claim 14.

20. A method of vaccinating a target against *Rhipicephalus* ticks, comprising administering to the target the vaccine of claim 13.

* * * * *